US 7,112,434 B2

(12) United States Patent
Cannon et al.

(10) Patent No.: US 7,112,434 B2
(45) Date of Patent: Sep. 26, 2006

(54) VECTOR SYSTEM FOR SELECTION OF GENES ENCODING SECRETED PROTEINS AND MEMBRANE-BOUND PROTEINS

(75) Inventors: John P. Cannon, St. Petersburg, FL (US); Robert N. Haire, Clearwater, FL (US); Gary W. Litman, Gulfport, FL (US)

(73) Assignee: University of South Florida, Tampa, FL (US)

( * ) Notice: Subject to any disclaimer, the term of this patent is extended or adjusted under 35 U.S.C. 154(b) by 316 days.

(21) Appl. No.: 10/138,998

(22) Filed: May 2, 2002

(65) Prior Publication Data

US 2003/0148299 A1 Aug. 7, 2003

Related U.S. Application Data

(60) Provisional application No. 60/288,046, filed on May 2, 2001.

(51) Int. Cl.
*C12N 15/00* (2006.01)
*C12N 15/64* (2006.01)
*C12N 15/66* (2006.01)
*C07H 21/02* (2006.01)

(52) U.S. Cl. ............... 435/320.1; 435/91.4; 435/91.41; 536/23.1; 536/24.1

(58) Field of Classification Search ............. 435/320.1, 435/91.4, 91.41, 91.42, 69.1, 440
See application file for complete search history.

(56) References Cited

U.S. PATENT DOCUMENTS

| | | | |
|---|---|---|---|
| 5,037,760 | A | 8/1991 | Smith et al. |
| 5,159,062 | A | 10/1992 | Knapp et al. |
| 5,525,486 | A | 6/1996 | Honjo et al. |
| 5,529,908 | A | 6/1996 | Palva et al. |
| 5,536,637 | A | 7/1996 | Jacobs |
| 5,624,826 | A | 4/1997 | Kato et al. |
| RE35,585 | E | 8/1997 | Fernandez-Pol |
| 5,674,703 | A | 10/1997 | Woo et al. |
| 5,710,027 | A | 1/1998 | Hauptmann et al. |
| 5,767,336 | A | 6/1998 | Skarnes |
| 5,783,442 | A | 7/1998 | Kato et al. |
| 5,789,653 | A | 8/1998 | Skarnes |
| 5,824,469 | A | 10/1998 | Horwitz et al. |
| 5,882,924 | A | 3/1999 | Fritz et al. |
| 5,891,855 | A * | 4/1999 | Florkiewicz .................. 514/26 |
| 5,952,171 | A * | 9/1999 | McCarthy et al. ............. 435/6 |
| 6,046,000 | A | 4/2000 | McCarthy et al. |
| 6,046,158 | A * | 4/2000 | Ariizumi et al. ............... 514/2 |
| 6,090,587 | A | 7/2000 | Rhodes et al. |
| 6,103,472 | A | 8/2000 | Thukral |
| 6,150,098 | A | 11/2000 | Zhang et al. |
| 6,180,391 | B1 | 1/2001 | Brown |
| 6,218,161 | B1 | 4/2001 | Tsuji et al. |
| 6,228,590 | B1 * | 5/2001 | Baker ............................ 435/6 |
| 2002/0127557 | A1 * | 9/2002 | Tan et al. ....................... 435/6 |

FOREIGN PATENT DOCUMENTS

| | | |
|---|---|---|
| DE | 3901681 A1 | 7/1990 |
| EP | 0 244 042 A1 | 11/1987 |
| EP | 0 731 169 A1 | 9/1996 |
| WO | WO 96/40904 A1 | 12/1996 |
| WO | WO 98/22491 A1 | 5/1998 |
| WO | WO 99/49028 A1 | 9/1999 |
| WO | WO 02/072821 A2 | 9/2002 |

OTHER PUBLICATIONS

Arca, B. et al. "Trapping cDNAs encoding secreted proteins from the salivary glands of the malaria vector *Anopheles gambiae*" *Proc. Natl. Acad. Sci. USA*, Feb. 1999, 96:1516-1521.
Chen, H. and Leder, P. "A new signal sequence trap using alkaline phosphatase as a reporter" *Nucleic Acids Research*, 1999, 27(4):1219-1222.
Chubb, A. et al. Identification of *Mycobacterium tuberculosis* signal sequences that direct the export of a leaderless β-lactamase gene product in *Escherichia coli Microbiology*, 1998, 144:1619-1629.
De Sutter, K. et al. "Disulphide bridge formation in the periplasm of *Escherichia coli*: β-lactamase::human IgG3 hinge fusions as a model system" *Molecular Microbiology*, 1992, 6(15):2201-2208.
Engels, J. and Uhlmann, E. "Gene Synthesis" *Angew. Chem. Int. Ed. Engl.*, 1969, 28:716-734.
Imai, T. et al. "Molecular Cloning of a Novel T Cell-Directed CC Chemokine Expressed in Thymus by Signal Sequence Trap Using Epstein-Barr Virus Vector" *Journal of Biological Chemistry*, 1996, 271(35):21514-21521.
Klein, R. et al. "Selection for genes encoding secreted proteins and receptors" *Proc. Natl. Acad. Sci. USA*, Jul. 1996, 93:7108-7113.
Kolmar, H. et al. General mutagenesis/gene expression procedure for the construction of variant immunoglobulin domains in *Escherichia coli J. Mol. Biol.*, 1992, 228:359-365.
Lee, M. et al. "Characterization of *Enterococcus faecalis* alkaline phosphatase and use in identifying *Streptococcus agalactiae* secreted proteins" *Journal of Bacteriology*, Sep. 1999, 181(18):5790-5799.
Palzkill, T, et al. "Selection of functional signal peptide cleavage sites from a library of random sequences" *Journal of Bacteriology*, Feb. 1994, 176(3):563-568.
Peterfy, M. et al. "Signal-exon trap: a novel method for the identification of signal sequences from genomic DNA" *Nucleic Acids Research*, 2000, vol. 28(7), e26, pp. I-vii.
Seehaus, T. et al. "A vector for the removal of deletion mutants from antibody libraries" *Gene*, 1992, 114:235-237.

(Continued)

*Primary Examiner*—Dave Trong Nguyen
*Assistant Examiner*—Maria Marvich
(74) *Attorney, Agent, or Firm*—Saliwanchik, Lloyd & Saliwanchik

(57) ABSTRACT

The subject invention concerns novel vectors for the rapid and robust selection for cDNA sequences that encode secreted or membrane-bound proteins. The invention also pertains to methods for cloning secreted or membrane-bound proteins, including proteins encoded by novel members of gene families.

6 Claims, 12 Drawing Sheets

OTHER PUBLICATIONS

Shirozu, M. et al. "Characterization of novel secreted and membrane proteins isolated by the signal sequence trap method" *Genomics*, 1996, 37:273-280.

Sibakov, M. et al. "Secretion of TEM β-lactamase with signal sequences isolated from the chromosome of *Lactococcus lactis* subsp. *lactis*" *Applied and Environmental Microbiology*, Feb. 1991, 57(2):341-348.

Tashiro, K. et al. "Signal sequence trap: A cloning strategy for secreted proteins and type 1 membrane proteins" *Science*, Jul. 30, 1993, 261:600-603.

Wells, J. et al. "Cassette mutagenesis: an efficient method for generation of multiple mutations at defined sites" *Gene*, 1985, 34:315-323.

Belin, D. et al. "Functional activity of eukaryotic signal sequences in *Escherichia coli*: the ovalburnin family of serine protease inhibitors" *J. Mol. Biol.*, 2004, 335:437-453.

Clontech, λTriplEx™ & λTriplEx2™ Libraries User Manual, published Oct. 2, 2000.

Persans, M. et al. "Molecular dissection of the role of histidine in nickel hyperaccumulation in *Thlaspi goesingense* (Hálácsy)" *Plant Physiology*, 1999, 121:1117-1126.

Wagner, L. et al. "Transcriptional slippage occurs during elongation at runs of adenine or thymine in *Escherichia coli*" *Nucleic Acids Res.*, 1990, 18:3529-3535.

\* cited by examiner

MCS = multiple cloning site
LacP = lac promoter

MCS = multiple cloning site
LacP = lac promoter

Coding for Figure 5:

Regular text = vector backbone
Bold text = neomycin phosphotransferase gene
Underlined text = lac promoter
Italicized text = multiple cloning sites
Bold and underlined text = signalless beta-lactamase gene Sequence of G7311------
GCACTTTTCGGGGAAATGTGCGCGGAACCCCTATTTGTTTATTTTTCTAAATACATTCAAATATGTATCCGCTCAT
GAGACAATAACCCTGATAAATGCTTCAATAATATTGAAAAGGAAGAGTCCTGAGGAAGCGAACCGGAATT
GCCAGCTGGGGCGCCCTCTGGTAAGGTTGGGAAGCCCTGCAAAGTAAACTGGATGGCTTTCT
GCCGCCAAGGATCTGATGGCGCAGGGGATCAAGCTCTGATCAAGAGACAGGATGAGGATCGTT
TCGCATGATTGAACAAGATGGATTGCACGCAGGTTCTCCGGCCGCTTGGGTGGAGAGGCTATT
CGGCTATGACTGGGCACAACAGACAATCGGCTGCTCTGATGCCGCCGTGTTCCGGCTGTCAGC
GCAGGGGCGCCCGGTTCTTTTTGTCAAGACCGACCTGTCCGGTGCCCTGAATGAACTGCAAGA
CGAGGCAGCGCGGCTATCGTGGCTGGCCACGACGGGCGTTCCTTGCGCAGCTGTGCTCGACGT
TGTCACTGAAGCGGGAAGGGACTGGCTGCTATTGGGCGAAGTGCCGGGGCAGGATCTCCTGTC
ATCTCACCTTGCTCCTGCCGAGAAAGTATCCATCATGGCTGATGCAATGCGGCGGCTGCATAC
GCTTGATCCGGCTACCTGCCCATTCGACCACCAAGCGAAACATCGCATCGAGCGAGCACGTAC
TCGGATGGAAGCCGGTCTTGTCGATCAGGATGATCTGGACGAAGAGCATCAGGGGCTCGCGCC
AGCCGAACTGTTCGCCAGGCTCAAGGCGAGCATGCCCGACGGCGAGGATCTCGTCGTGACCCA
TGGCGATGCCTGCTTGCCGAATATCATGGTGGAAAATGGCCGCTTTTCTGGATTCATCGACTG
TGGCCGGCTGGGTGTGGCGGACCGCTATCAGGACATAGCGTTGGCTACCCGTGATATTGCTGA
AGAGCTTGGCGGCGAATGGGCTGACCGCTTCCTCGTGCTTTACGGTATCGCCGCTCCCGATTC
GCAGCGCATCGCCTTCTATCGCCTTCTTGACGAGTTCTTCTGAATTATTAACGCTTACAATTT
CCTGATGCGGTATTTTCTCCTTACGCATCTGTGCGGTATTTCACACCGCATACAGGTGGCACT
TTTCGGGGAAATGTGCGCGGAACCCCCTCAGGTTACTCATATATACTTTAGATTGATTTAAAACTTCATT
TTTAATTTAAAAGGATCTAGGTGAAGATCCTTTTTGATAATCTCATGACCAAAATCCCTTAACGTGAGTTTTCGTT
CCACTGAGCGTCAGACCCCGTAGAAAAGATCAAAGGATCTTCTTGAGATCCTTTTTTTCTGCGCGTAATCTGCTGC
TTGCAAACAAAAAAACCACCGCTACCAGCGGTGGTTTGTTTGCCGGATCAAGAGCTACCAACTCTTTTTCCGAAGG
TAACTGGCTTCAGCAGAGCGCAGATACCAAATACTGTCCTTCTAGTGTAGCCGTAGTTAGGCCACCACTTCAAGAA
CTCTGTAGCACCGCCTACATACCTCGCTCTGCTAATCCTGTTACCAGTGGCTGCTGCCAGTGGCGATAAGTCGTGT
CTTACCGGGTTGGACTCAAGACGATAGTTACCGGATAAGGCGCAGCGGTCGGGCTGAACGGGGGGTTCGTGCACAC
AGCCCAGCTTGGAGCGAACGACCTACACCGAACTGAGATACCTACAGCGTGAGCTATGAGAAAGCGCCACGCTTCC
CGAAGGGAGAAAGGCGGACAGGTATCCGGTAAGCGGCAGGGTCGGAACAGGAGAGCGCACGAGGGAGCTTCCAGGG
GGAAACGCCTGGTATCTTTATAGTCCTGTCGGGTTTCGCCACCTCTGACTTGAGCGTCGATTTTTGTGATGCTCGT
CAGGGGGGCGGAGCCTATGGAAAAACGCCAGCAACGCGGCCTTTTTACGGTTCCTGGCCTTTTGCTGGCCTTTTGC
TCACATGTTCTTTCCTGCGTTATCCCCTGATTCTGTGGATAACCGTATTACCGCCATGCATTAGTTATTAATAGTA
ATCAATTACGGGGTCATTAGTTCATAGCCCATATATGGAGTTCCGCGTTACATAACTTACGGTAAATGGCCCGCCT
GGCTGACCGCCCAACGACCCCCGCCCATTGACGTCAATAATGACGTATGTTCCCATAGTAACGCCAATAGGGACTT
TCCATTGACGTCAATGGGTGGAGTATTTACGGTAAACTGCCCACTTGGCAGTACATCAAGTGTATCATATGCCAAG
TACGCCCCCTATTGACGTCAATGACGGTAAATGGCCCGCCTGGCATTATGCCCAGTACATGACCTTATGGGACTTT
CCTACTTGGCAGTACATCTACGTATTAGTCATCGCTATTACCATGGTGATGCGGTTTTGGCAGTACATCAATGGGC
GTGGATAGCGGTTTGACTCACGGGGATTTCCAAGTCTCCACCCCATTGACGTCAATGGGAGTTTGTTTTGGCACCA
AAATCAACGGGACTTTCCAAAATGTCGTAACAACTCCGCCCCATTGACGCAAATGGGCGGTAGGCGTGTACGGTGG
GAGGTCTATATAAGCAGAGCTGGTTTAGTGAACCGTCAGATCCGCTAGCCGCAATTACTGTGAGTTAGCT
<u>CACTCATTAGGCACCCCAGGCTTTACACTTTATACTTCCGGCTCGTATATTGTGTGGAATTGT</u>
<u>GAGCGGATAACAATTTCACACAGGAAACAGCT</u>*ATGACCTTGATTACGCCAAGCTCGAAATTAACCCTCAC*
*TAAAGGGAACAAAAGCTG*GAGCTCCACCGCGGATTGATAGTAAGGCCATTATGGCCGAATTCGGCC
*GCCTCGGCCGGATCCCCCGGGCTGCAG*GAATTCGCACCCAGAAACGCTGGTGAAAGTAAAAGAT
GCTGAAGATCAGTTGGGTGCACGAGTGGGTTACATCGAACTGGATCTCAACAGCGGTAAGATC
CTTGAGAGTTTTCGC

FIG. 5A

```
CCCGAAGAACGTTTTCCAATGATGAGCACTTTTAAAGTTCTGCTATGTGGCGCGGTATTATCC
CGTATTGACGCCGGGCAAGAGCAACTCGGTCGCCGCATACACTATTCTCAGAATGACTTGGTT
GAGTACTCACCAGTCACAGAAAAGCATCTTACGGATGGCATGACAGTAAGAGAATTATGCAGT
GCTGCCATAACCATGAGTGATAACACTGCGGCCAACTTACTTCTGACAACGATCGGAGGACCG
AAGGAGCTAACCGCTTTTTTGCACAACATGGGGGATCATGTAACTCGCCTTGATCGTTGGGAA
CCGGAGCTGAATGAAGCCATACCAAACGACGAGCGTGACACCACGATGCCTGTAGCAATGGCA
ACAACGTTGCGCAAACTATTAACTGGCGAACTACTTACTCTAGCTTCCCGGCAACAATTAATA
GACTGGATGGAGGCGGATAAAGTTGCAGGACCACTTCTGCGCTCGGCCCTTCCGGCTGGCTGG
TTTATTGCTGATAAATCTGGAGCCGGTGAGCGTGGGTCTCGCGGTATCATTGCAGCACTGGGG
CCAGATGGTAAGCCCTCCCGTATCGTAGTTATCTACACGACGGGGAGTCAGGCAACTATGGAT
GAACGAAATAGACAGATCGCTGAGATAGGTGCCTCACTGATTAAGCATTGGTAAGAATTCGATAT
CAAGCTTATAACTTCGTATAGCAGCATACATTATACGAAGTTATCTCGAGGGGGGCCCGGTACCAGGTAAGTGTA
CCCAATTCGCCCTATAGTGAGTCGTATTACAATTCACTGGCCGTCGTTTTACAACGTCGTGACTGGGAAAACCCTG
GCGTTACCCAACTTAATCGCCTTGCAGCACATCCCCCTTTCGCCAGCTGGCGTAATAGCGAAGAGGCCCGCACCGA
TCGCCCTTCCCAACAGTTGCGCAGCCTGAATGGCGAATGGAGATCCAATTTTTAAGTGTATAATGTGTTAAACTAC
TGATTCTAATTGTTTGTGTATTTTAGATTCACAGTCCCAAGGCTCATTTCAGGCCCCTCAGTCCTCACAGTCTGTT
CATGATCATAATCAGCCATACCACATTTGTAGAGGTTTTACTTGCTTTAAAAAACCTCCCACACCTCCCCCTGAAC
CTGAAACATAAAATGAATGCAATTGTTGTTGTTAACTTGTTTATTGCAGCTTATAATGGTTACAAATAAAGCAATA
GCATCACAAATTTCACAAATAAAGCATTTTTTTCACTGCATTCTAGTTGTGGTTTGTCCAAACTCATCAATGTATC
TTAACGCGTAAATTGTAAGCGTTAATATTTTGTTAAAATTCGCGTTAAATTTTGTTAAATCAGCTCATTTTTTAA
CCAATAGGCCGAAATCGGCAAAATCCCTTATAAATCAAAAGAATAGACCGAGATAGGGTTGAGTGTTGTTCCAGTT
TGGAACAAGAGTCCACTATTAAAGAACGTGGACTCCAACGTCAAAGGGCGAAAAACCGTCTATCAGGGCGATGGCC
CACTACGTGAACCATCACCCTAATCAAGTTTTTTGGGGTCGAGGTGCCGTAAAGCACTAAATCGGAACCCTAAAGG
GAGCCCCCGATTTAGAGCTTGACGGGGAAAGCCGGCGAACGTGGCGAGAAAGGAAGGGAAGAAAGCGAAAGGAGCG
GCGCTAGGGCGCTGGCAAGTGTAGCGGTCACGCTGCGCGTAACCACCACACCCGCCGCGCTTAATGCGCCGCTAC
AGGGCGCGTCAGGTG
```

FIG. 5B

Coding for Figure 6:

Regular text = vector backbone
Bold text = neomycin phosphotransferase gene
Underlined text = lac promoter
*Italicized text = multiple cloning sites*
*Italicized and underlined text = SLIP sequence*
Bold and underlined text = signalless beta-lactamase gene

Sequence of G7637------
GCACTTTTCGGGGAAATGTGCGCGGAACCCCTATTTGTTTATTTTTCTAAATACATTCAAATATGTATCCGCTCAT
GAGACAATAACCCTGATAAATGCTTCAATAATATTGAAAAAGGAAGAGTCCTGAGGAAGCGAACCGGAATT
GCCAGCTGGGGCGCCCTCTGGTAAGGTTGGGAAGCCCTGCAAAGTAAACTGGATGGCTTTCTC
GCCGCCAAGGATCTGATGGCGCAGGGGATCAAGCTCTGATCAAGAGACAGGATGAGGATCGTT
TCGCATGATTGAACAAGATGGATTGCACGCAGGTTCTCCGGCCGCTTGGGTGGAGAGGCTATT
CGGCTATGACTGGGCACAACAGACAATCGGCTGCTCTGATGCCGCCGTGTTCCGGCTGTCAGC
GCAGGGGCGCCCGGTTCTTTTTGTCAAGACCGACCTGTCCGGTGCCCTGAATGAACTGCAAGA
CGAGGCAGCGCGGCTATCGTGGCTGGCCACGACGGGCGTTCCTTGCGCAGCTGTGCTCGACGT
TGTCACTGAAGCGGGAAGGGACTGGCTGCTATTGGGCGAAGTGCCGGGGCAGGATCTCCTGTC
ATCTCACCTTGCTCCTGCCGAGAAAGTATCCATCATGGCTGATGCAATGCGGCGGCTGCATAC
GCTTGATCCGGCTACCTGCCCATTCGACCACCAAGCGAAACATCGCATCGAGCGAGCACGTAC
TCGGATGGAAGCCGGTCTTGTCGATCAGGATGATCTGGACGAAGAGCATCAGGGGCTCGCGCC
AGCCGAACTGTTCGCCAGGCTCAAGGCGAGCATGCCCGACGGCGAGGATCTCGTCGTGACCCA
TGGCGATGCCTGCTTGCCGAATATCATGGTGGAAAATGGCCGCTTTTCTGGATTCATCGACTG
TGGCCGGCTGGGTGTGGCGGACCGCTATCAGGACATAGCGTTGGCTACCCGTGATATTGCTGA
AGAGCTTGGCGGCGAATGGGCTGACCGCTTCCTCGTGCTTTACGGTATCGCCGCTCCCGATTC
GCAGCGCATCGCCTTCTATCGCCTTCTTGACGAGTTCTTCTGAATTATTAACGCTTACAATTT
CCTGATGCGGTATTTTCTCCTTACGCATCTGTGCGGTATTTCACACCGCATACAGGTGGCACT
TTTCGGGGAAATGTGCGCGGAACCCCCTCAGGTTACTCATATATACTTTAGATTGATTTAAAACTTCATT
TTTAATTTAAAAGGATCTAGGTGAAGATCCTTTTTGATAATCTCATGACCAAAATCCCTTAACGTGAGTTTTCGTT
CCACTGAGCGTCAGACCCCGTAGAAAAGATCAAAGGATCTTCTTGAGATCCTTTTTTTCTGCGCGTAATCTGCTGC
TTGCAAACAAAAAAACCACCGCTACCAGCGGTGGTTTGTTTGCCGGATCAAGAGCTACCAACTCTTTTTCCGAAGG
TAACTGGCTTCAGCAGAGCGCAGATACCAAATACTGTCCTTCTAGTGTAGCCGTAGTTAGGCCACCACTTCAAGAA
CTCTGTAGCACCGCCTACATACCTCGCTCTGCTAATCCTGTTACCAGTGGCTGCTGCCAGTGGCGATAAGTCGTGT
CTTACCGGGTTGGACTCAAGACGATAGTTACCGGATAAGGCGCAGCGGTCGGGCTGAACGGGGGGTTCGTGCACAC
AGCCCAGCTTGGAGCGAACGACCTACACCGAACTGAGATACCTACAGCGTGAGCTATGAGAAAGCGCCACGCTTCC
CGAAGGGAGAAAGGCGGACAGGTATCCGGTAAGCGGCAGGGTCGGAACAGGAGAGCGCACGAGGGAGCTTCCAGGG
GGAAACGCCTGGTATCTTTATAGTCCTGTCGGGTTTCGCCACCTCTGACTTGAGCGTCGATTTTTGTGATGCTCGT
CAGGGGGGCGGAGCCTATGGAAAAACGCCAGCAACGCGGCCTTTTTACGGTTCCTGGCCTTTTGCTGGCCTTTTGC
TCACATGTTCTTTCCTGCGTTATCCCCTGATTCTGTGGATAACCGTATTACCGCCATGCATTAGTTATTAATAGTA
ATCAATTACGGGGTCATTAGTTCATAGCCCATATATGGAGTTCCGCGTTACATAACTTACGGTAAATGGCCCGCCT
GGCTGACCGCCCAACGACCCCCGCCCATTGACGTCAATAATGACGTATGTTCCCATAGTAACGCCAATAGGGACTT
TCCATTGACGTCAATGGGTGGAGTATTTACGGTAAACTGCCCACTTGGCAGTACATCAAGTGTATCATATGCCAAG
TACGCCCCCTATTGACGTCAATGACGGTAAATGGCCCGCCTGGCATTATGCCCAGTACATGACCTTATGGGACTTT
CCTACTTGGCAGTACATCTACGTATTAGTCATCGCTATTACCATGGTGATGCGGTTTTGGCAGTACATCAATGGGC
GTGGATAGCGGTTTGACTCACGGGGATTTCCAAGTCTCCACCCCATTGACGTCAATGGGAGTTTGTTTTGGCACCA
AAATCAACGGGACTTTCCAAAATGTCGTAACAACTCCGCCCCATTGACGCAAATGGGCGGTAGGCGTGTACGGTGG
GAGGTCTATATAAGCAGAGCTGGTTTAGTGAACCGTCAGATCCGCTAGCCGCAATTACTGTGAGTTAGCT
CACTCATTAGGCACCCCAGGCTTTACACTTTATACTTCCGGCTCGTATATTGTGTGGAATTGT
GAGCGGATAACAATTTCACACAGGAAACAGCTATGACCTTGATTACGCCAAGCTCGAAATTAACCCTCAC
TAAAGGGAACAAAAGCTG*GAGCTCCACCGCGGATTGATAGTAAGGCCATTATGGCCGAATTCGGCC*
*GCCTCGGCCGGATCCAATTTTTTTTTTTT*GGAATTCGCACCCAGAAACGCTGGTGAAAGTAAAAGA

FIG. 6A

```
TGCTGAAGATCAGTTGGGTGCACGAGTGGGTTACATCGAACTGGATCTCAACAGCGGTAAGAT
CCTTGAGAGTTTTCGCCCCGAAGAACGTTTTCCAATGATGAGCACTTTTAAAGTTCTGCTATG
TGGCGCGGTATTATCCCGTATTGACGCCGGGCAAGAGCAACTCGGTCGCCGCATACACTATTC
TCAGAATGACTTGGTTGAGTACTCACCAGTCACAGAAAGCATCTTACGGATGGCATGACAGT
AAGAGAATTATGCAGTGCTGCCATAACCATGAGTGATAACACTGCGGCCAACTTACTTCTGAC
AACGATCGGAGGACCGAAGGAGCTAACCGCTTTTTTGCACAACATGGGGGATCATGTAACTCG
CCTTGATCGTTGGGAACCGGAGCTGAATGAAGCCATACCAAACGACGAGCGTGACACCACGAT
GCCTGTAGCAATGGCAACAACGTTGCGCAAACTATTAACTGGCGAACTACTTACTCTAGCTTC
CCGGCAACAATTAATAGACTGGATGGAGGCGGATAAAGTTGCAGGACCACTTCTGCGCTCGGC
CCTTCCGGCTGGCTGGTTTATTGCTGATAAATCTGGAGCCGGTGAGCGTGGGTCTCGCGGTAT
CATTGCAGCACTGGGGCCAGATGGTAAGCCCTCCCGTATCGTAGTTATCTACACGACGGGGAG
TCAGGCAACTATGGATGAACGAAATAGACAGATCGCTGAGATAGGTGCCTCACTGATTAAGCA
TTGGTAAGAATTCGATATCAAGCTTATAACTTCGTATAGCAGCATACATTATACGAAGTTATCTCGAGGGGGGC
CCGGTACCAGGTAAGTGTACCCAATTCGCCCTATAGTGAGTCGTATTACAATTCACTGGCCGTCGTTTTACAACGT
CGTGACTGGGAAAACCCTGGCGTTACCCAACTTAATCGCCTTGCAGCACATCCCCCTTTCGCCAGCTGGCGTAATA
GCGAAGAGGCCCGCACCGATCGCCCTTCCCAACAGTTGCGCAGCCTGAATGGCGAATGGAGATCCAATTTTTAAGT
GTATAATGTGTTAAACTACTGATTCTAATTGTTTGTGTATTTTAGATTCACAGTCCCAAGGCTCATTTCAGGCCCC
TCAGTCCTCACAGTCTGTTCATGATCATAATCAGCCATACCACATTTGTAGAGGTTTTACTTGCTTTAAAAAACCT
CCCACACCTCCCCCTGAACCTGAAACATAAAATGAATGCAATTGTTGTTGTTAACTTGTTTATTGCAGCTTATAAT
GGTTACAAATAAAGCAATAGCATCACAAATTTCACAAATAAAGCATTTTTTTCACTGCATTCTAGTTGTGGTTTGT
CCAAACTCATCAATGTATCTTAACGCGTAAATTGTAAGCGTTAATATTTTGTTAAAATTCGCGTTAAATTTTTGTT
AAATCAGCTCATTTTTTAACCAATAGGCCGAAATCGGCAAAATCCCTTATAAATCAAAAGAATAGACCGAGATAGG
GTTGAGTGTTGTTCCAGTTTGGAACAAGAGTCCACTATTAAAGAACGTGGACTCCAACGTCAAAGGGCGAAAAACC
GTCTATCAGGGCGATGGCCCACTACGTGAACCATCACCCTAATCAAGTTTTTTGGGGTCGAGGTGCCGTAAAGCAC
TAAATCGGAACCCTAAAGGGAGCCCCCGATTTAGAGCTTGACGGGGAAAGCCGGCGAACGTGGCGAGAAAGGAAGG
GAAGAAAGCGAAAGGAGCGGGCGCTAGGGCGCTGGCAAGTGTAGCGGTCACGCTGCGCGTAACCACCACACCCGCC
GCGCTTAATGCGCCGCTACAGGGCGCGTCAGGTG
```

FIG. 6B

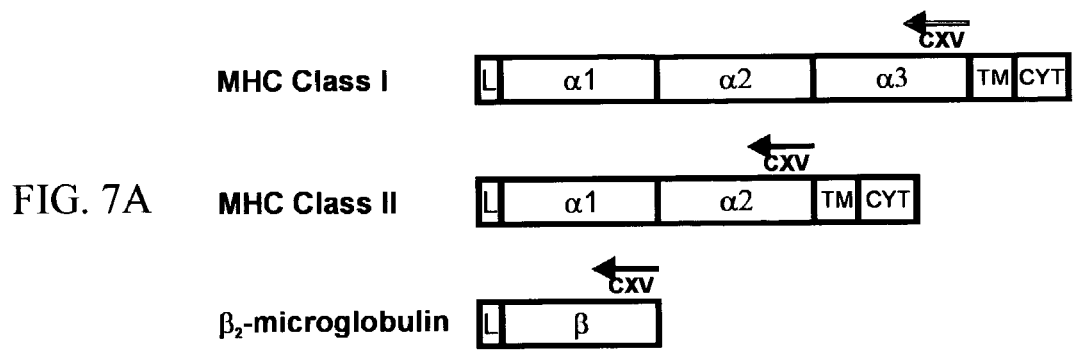
FIG. 7A
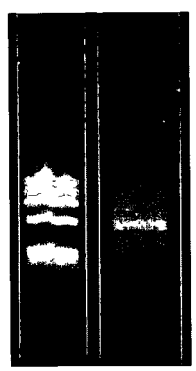
FIG. 7B
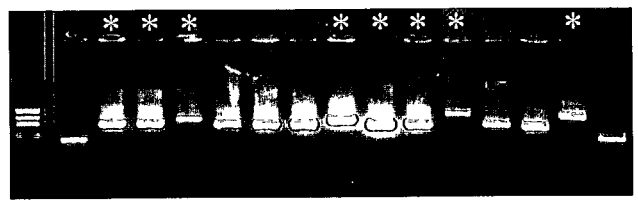
FIG. 7C
| Lane # | Sequence |
|---|---|
| 2 | MHC Class II |
| 3 | MHC Class II |
| 4 | (novel sequence) |
| 8 | MHC Class II |
| 9 | MHC Class II |
| 10 | MHC Class II |
| 11 | connective tissue growth factor-related |
| 14 | connective tissue growth factor-related |
FIG. 7D

```
V-CBP3     1  ------MQMFLINSVCLGMAYGQSIMTVRTTHTEVEVHAG--------GTVELPCAYQIA
V-CBP1     1  ------MKFVLGIVLLAVGAHAMTIVVSTPEPKVEASVG---------GSAELKCEFDIQ
V-CBP2     1  MLGLLVAISAVAVACFESSYADAVSITNVTAPYRGSWVMWNTWDPTWNRVEIGCEYTIS

V-CBP3    47  N-DTQPPVISWLKGARRTEAPRSSRETTGRERGWGSWRATDKESFGDFTGRASVANLAA
V-CBP1    47  PNSTQPPTIAWFKGN---DDFRGVERIYTG-HKVWGNETERREDSFGDYTGRVEVADLDK
V-CBP2    61  PAPATPPTIEWLKGS---------------FIDRQVLKLTSSGEVYVHPEYAGRVSVPSRTH

V-CBP3   106  PTLRLTHVHPQDGGRYWCQVAQWSIRTEFGIDAKS--VVLKVTGHTPSNNVHVSTAEVVQ-
V-CBP1   103  PAIKISGIKSTDFARYWCTVAEWGVRTELGVDAKS--VLTETGHSEAS-LDISVSGEKD-
V-CBP2   109  PTLVLTDSKFDDWGRYWCRVTNEEQSDDFGTDEESRLFWFKSGYDPARGSHYSFVQDKT

V-CBP3   164  ------VDEGNDITMTCPCTDCANANVTWYTGPIFF--------ENYETGTYQPIPTRTSSASP
V-CBP1   160  ------VEEGGDVEMTCRCHGCTSAAIFDWFKGAFAGS------EWTIGNYTHIAAKVDVGVL
V-CBP2   169  PVRVKTGGTAKLHCEGWGGKSASIVWEKGPSCTQDGNCNVYEWVINKTAVEHFSPDPGEV

V-CBP3   214  GSRLRSRAGRASAARGTWSSGPPRST-----DAGRVWCELATGQGEL----DADRSTEL
V-CBP1   212  GFPNPIEIDDEFGQFSVTPSNSLRITGAQVADAGRYWCKVTSGGS------VDIKATVL
V-CBP2   229  NVSPNYAGRASLGANNMGYTLDLTTDIRPADVGRYWCTNDWPLYFRNEVQSRDSQSVVV

V-CBP3   265  KVQLEPFTCDGKPTGEYADPTACDYYYQCIPGKP-PLHRPCGYAGMVFNEEMQYCDWDIN
V-CBP1   265  KVKVPFTCAGKADGYPPDEDCAMYYQCLYGFPQPFHRPCGYAGMVFNPEHLYCDWAFN
V-CBP2   289  LDDEAPSCDGKADGMYQDPGDCSRYYTCSGGWL--VGPVPCISGIFFNEALQVCDWPNN

V-CBP3   324  VPPPCGSKPV
V-CBP1   325  VGPPCGSKA-
V-CBP2   347  VACV------
```

FIG. 9B

VECTOR SYSTEM FOR SELECTION OF GENES ENCODING SECRETED PROTEINS AND MEMBRANE-BOUND PROTEINS

CROSS-REFERENCE TO RELATED APPLICATION(S)

This application claims the benefit of provisional patent application Ser. No. 60/288,046, filed May 2, 2001, which is hereby incorporated by reference in its entirety, including all nucleic acid sequences, amino acid sequences, figures, tables, and drawings.

The subject invention was made with government support under a research project supported by National Institutes of Health Grant No. AI23338. The government may have certain rights in this invention.

BACKGROUND OF THE INVENTION

Proteins destined for transport into or across cell membranes are usually translated with a signal sequence that directs the newly synthesized protein to the appropriate membrane translocation system. The primary structure of signal sequences is highly variable among different proteins. Signal sequences that target proteins for export from the cytosol generally contain a short stretch (7–20 residues) of hydrophobic amino acids. In most cases, the signal sequence is located at the amino terminus of a nascent protein and is proteolytically removed on the trans side of the membrane (e.g. lumen of endoplasmic reticulum, bacterial periplasm, intercisternal space of mitochondria and chloroplasts), although examples of mature proteins containing uncleaved or internal signal sequences have been described. Export signal sequences may be interchanged among different proteins, even proteins of different species of organisms.

Many secreted proteins interact with target cells to bring about physiological responses such as growth, differentiation and/or activation. These activities make secreted proteins biologically interesting molecules that are potentially valuable as therapeutics or as targets for ligands. Of the estimated 60,000 to 100,000 human genes, about 25% carry a signal peptide and about 4% are secreted extracellularly. Clearly, approaches to rapidly and accurately identifying secreted proteins are important components of gene-based drug discovery programs.

With advances in techniques for sequencing cDNAs, many expressed sequence tags (ESTs) have been generated which have enhanced the process of identifying novel secreted proteins as compared to the conventional reverse genetics approaches. However, ESTs are small random cDNA sequences and thus it becomes hard to identify secretion signal sequence that is normally present in the 5' end of cDNA encoding secreted protein. Moreover, after an EST carrying a potential secretion signal sequence is identified based on the homology search, it has to be authenticated in a functional assay. Thus a means for selection for the biochemical function of the proteins encoded by inserted cDNA would greatly simplify the process of obtaining novel secreted genes.

Secretion signal trap is one such method to clone 5' ends of cDNAs encoding secreted proteins from a random cDNA library. Generally, signal trapping relies on secretion of a reporter polypeptide by signal sequences present in a cDNA library. The secreted reporter polypeptide may then be detected by a variety of assays based upon, for example, growth selection, enzymatic activity, or immune reactivity. Examples of signal trap cloning procedures include those in U.S. Pat. No. 5,536,637 and Klein et al. *Proc. Natl. Acad. Sci. USA* 93, 7108–13 (1996), which describe signal trap cloning in yeast using the yeast invertase polypeptide as a reporter. Furthermore, Imai et al. *J. Biol. Chem.* 271, 21514–21 (1996) describes signal trap cloning in mammalian cells using CD4 as a reporter and identifying signal sequences by screening for surface expression of CD4 antigen. In addition, U.S. Pat. No. 5,525,486, Shirozu et al. *Genomics* 37, 273–80 (1996) and Tashiro et al. *Science* 261, 600–03 (1993) describe signal trap cloning in mammalian cells and identify signal sequences by screening for surface expression of IL-2 receptor fusion proteins. None of these references teaches cloning in prokaryotic cells.

Signal sequence trapping using mammalian cells has disadvantages, including low transfection efficiency, relatively expensive culture medium, and difficult recovery of vector-borne cDNA sequences from cells that have been transfected. Signal sequence trapping using yeast cells also has the disadvantage of slow growth time as compared to bacterial cells. Further, methods for molecular cloning in yeast cells are generally more complicated than bacterial methods. By contrast, bacterial cells have the advantages of fast doubling times, high transformation efficiencies, and ease of use, as compared to both mammalian and yeast cells, accommodating a wider range of experience levels in the laboratory.

U.S. Pat. No. 5,037,760 describes signal trap cloning in *Bacillus* using α-amylase and β-lactamase as reporter genes. This patent teaches vectors for identifying secretory signal sequences from DNA fragments of unicellular microorganisms. It does not teach identifying signal sequences in complex eukaryotic organisms.

Sibakov et al. (1991) *Appl. Environ. Microbiol.* 57: 341–48 and Chubb et al. (1998) *Microbiology* 144: 1619–29 describe cloning of prokaryotic signal sequences using β-lactamase fusions. Sibakov, et al. and Chubb, et al. do not describe a screening strategy for detection of eukaryotic signal sequences using selection in a prokaryotic system.

Kolmar et al. (1992) *J. Mol. Biol.* 228: 359–365, Seehaus et al *Gene* 114: 235–37, Sutter et al. *Mol. Microbiol.* 6: 2201–2208, and Palzkill et al. (1994) *J. Bacteriol.* 176: 563–68 utilize β-lactamase fusions in the study of specific biological processes rather than as a means of cloning novel cDNAs on a large scale.

Chen and Leder (1999) *Nucleic Acids Res.* 27: 1219–22 and Lee et al. (1999) *J. Bacteriol.* 181: 5790–99 utilize color change from alkaline phosphatase activity during colony formation as a screening mechanism. Thus, a subjective determination of color changes is required for selection using these systems.

Although many of the above references describe the utility of fusions of various cDNA sequences to a β-lactamase sequence, none present a library-screening strategy for detection of eukaryotic signal sequences using selection in a prokaryotic system. Further, none of the aforementioned systems incorporate a single, degenerate primer-based polymerase chain reaction (PCR) strategy designed to clone novel gene family members.

Thus, there is a need to develop alternative approaches for rapid and accurate identification of novel secreted eukaryotic proteins using bacterial host cells.

BRIEF SUMMARY OF THE INVENTION

The present invention relates to a vector system that allows rapid and robust selection for cDNA sequences that encode secreted or membrane-bound proteins. More particularly, the present invention pertains to vectors comprising a reporter gene (such as β-lactamase) lacking a functional signal sequence; a selectable marker gene (such as neomycin phosphotransferase), wherein the reporter gene and selectable marker gene are operably linked to a promoter sequence (such as the lac promoter); and a multiple cloning site. Optionally, the vectors of the subject invention can further comprise a SLIP sequence, a plurality of thymidine nucleotides that allows for all three frames of any cloned cDNA to be fused to the reporter gene, thereby increasing the efficiency of cloning cDNAs for secreted or membrane-bound proteins.

The invention also relates to a method for cloning novel members of a gene family using plasmid vectors of the present invention. The method includes providing a vector of the subject invention. Preferably, the vector is linearized. The vector can be linearized, for example, with one or more restriction enzymes in order to produce a "sticky end" for ligation to a candidate nucleic acid sequence encoding a potential secreted or membrane-bound protein. The vector comprises DNA encoding a reporter gene lacking a functional signal sequence. The method further includes cutting the candidate nucleic acid sequence with one or more restriction enzymes in order to produce a compatible "sticky end" for ligation to the linearized vector and ligating the candidate nucleic acid sequence to the linearized vector, thereby forming a ligation product. Bacterial cells can then be transformed with the ligation product and colonies can be selected based on expression of the reporter gene functionally linked to the gene encoding the secreted or membrane-bound protein. The method can further include determining the nucleic acid sequence within the transformants from the selected colonies and determining the amino acid sequence based on the nucleic acid sequence.

In order to improve the overall efficiency of cloning of cDNAs that encode secreted proteins or membrane-bound proteins (such as membrane-bound receptors), as well as to identify homologous genes possessing only minimal sequence relatedness, the present inventors have engineered unique plasmid-based selection vectors and developed a cloning strategy that utilizes such vectors, wherein only minimal information about the gene of interest is necessary. This cloning strategy has been validated with a number of known members of the Ig superfamily (IgSF) and has led to the identification of a novel V region-containing, presumably bifunctional gene in amphioxus (*Branchiostoma floridae*), a protochordate (cephalochordate) species that lacks an adaptive immune system.

BRIEF DESCRIPTION OF THE DRAWINGS

The following is a brief description of the drawings that are presented only for the purposes of further illustrating the invention and not for the purposes of limiting same.

FIGS. 5A and 5B show the complete gene sequence of an Amptrap vector G7311 (SEQ ID NO:1) of the present invention.

FIGS. 6A and 6B show the complete gene sequence of an Amptrap vector G7637 (SEQ ID NO:2) of the present invention.

FIGS. 7A–7D show a strategy for cloning of *R. eglanteria* MHC Class II. FIG. 7A shows a priming strategy based on two conserved codon positions that occur in MHC I, MHC II and β2m. FIG. 7B shows agarose gel analysis of the 5'-RACE PCR products; size standard is ΦX174/Hae III. FIG. 7C shows the sizing of inserts from ampicillin resistant colonies. FIG. 7D shows the results of sequencing of eight size-selected clones. (*) indicates products selected for sequencing; size standard indicated.

FIGS. 8A–8E show the cloning of a novel IgSF gene from *B. floridae*. FIG. 8A shows sequence motifs that served as a basis for primer design. FIG. 8B (1–7) shows agarose gel analysis of 5'-RACE PCR products that were formed using individual Amptrap primers; (8) of FIG. 8B is a product formed with only a 5' primer (SMART-DNA primer: 5'-AAGCAGTGGTATCAACGCAGAGT-3' (SEQ ID NO. 7)); (6) of FIG. 8B is a size standard. FIG. 8C shows sizing of inserts from ampicillin resistant colonies by PCR; (*) indicates products selected for sequencing, note the length variation in products. FIG. 8D shows a schematic of amplicon G7977, containing a partial Ig-encoding sequence. FIG. 8E shows a schematic of full-length cDNA G9119.

FIGS. 9A–9E show structural aspects of a V region-containing chitin binding protein (V-CBP) and the presence of V-CBP1 mRNA in *B. floridae*. FIG. 9A shows, a schematic representation of V-CBP. FIG. 9B shows a ClustalW alignment of the three V-CBP proteins described herein (SEQ ID NOs. 3–5). FIG. 9C–9E show in situ hybridization to mRNA in serial transverse sections of adult *B. floridae* intestine. FIG. 9C shows hematoxylin and eosin staining. FIG. 9D shows in situ hybridization using a antisense RNA probe corresponding to V-CBP1 (note staining in scattered cells). FIG. 9E shows in situ hybridization using a sense (control) RNA probe corresponding to V-CBP1.

BRIEF DESCRIPTION OF THE SEQUENCES

Figure 1:
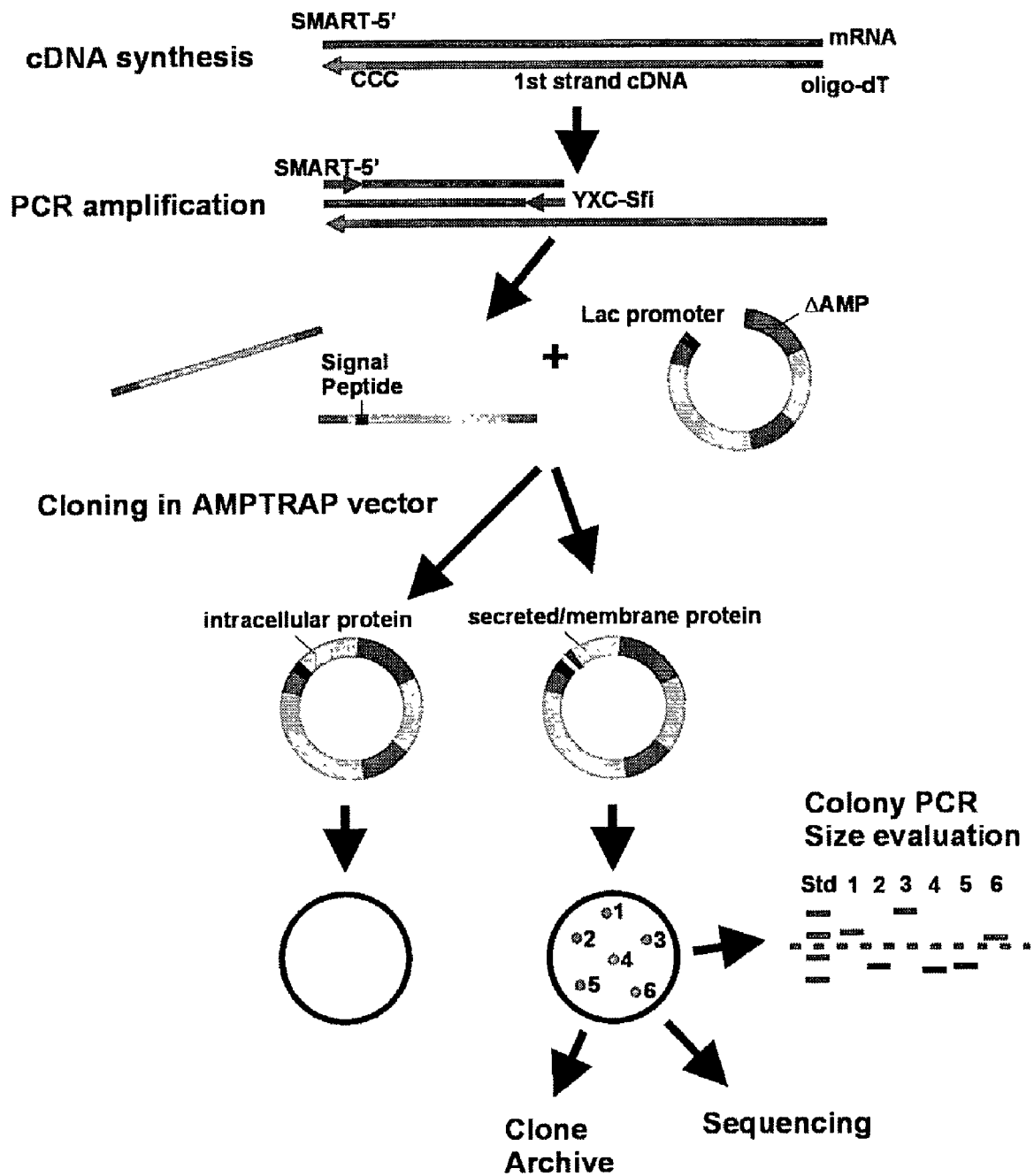
FIG. 1 outlines a strategy for the cloning of novel members of a gene family using the plasmid vector G7311 of the present invention. First-strand cDNA is synthesized using the SMART system (CLONTECH). First strand synthesis is performed in the presence of an oligoribonucleotide, SMART-5', that anneals to a nontemplated stretch of oligo (dC) residues added by reverse transcriptase (RT) to the end of the nascent cDNA. The RT enzyme completes the first strand of cDNA by adding nucleotides complementary to the SMART sequence. Polymerase chain reaction (PCR) is then performed on the cDNA using (1) an oligonucleotide corresponding to the SMART-5' sequence, which contains an SfiI recognition sequence (5'-GGCCNNNN^NGGCC (SEQ ID NO. 6)) and (2) a degenerate oligonucleotide, e.g., YXC-Sfi, corresponding to a putative conserved motif of three to five amino acids plus an SfiI recognition sequence. The SfiI sites in the PCR primers are asymmetric and allow directional cloning of PCR products into the Amptrap vector at corresponding SfiI sites. After selection of *E. coli* transformants on ampicillin, colonies can be evaluated for insert size using colony PCR. Inserts of the anticipated size range can be sequenced directly, and the source colonies can be archived for future use.

SEQ ID NO. 1 is the nucleotide sequence (G7311) of a vector of the subject invention.

SEQ ID NO. 2 is the nucleotide sequence (G7637) of a vector of the subject invention.

SEQ ID NOs. 3–5 are portions of V-CBP proteins, as shown in the CrustalW alignment in FIG. 9B.

SEQ ID NO. 6 is the recognition sequence of the SfiI endonuclease.

SEQ ID NOs. 7–15 are primers that were utilized to identify new proteins, using the methods of the subject invention.

DETAILED DISCLOSURE OF THE INVENTION

The present invention relates to a vector system that allows rapid and robust selection for cDNA sequences that encode secreted or membrane-bound proteins even when gene families are highly divergent and share only limited regions of sequence identity.

The present invention pertains to vectors comprising a reporter gene (such as β-lactamase) lacking a functional signal sequence; a selectable marker gene (such as neomycin phosphotransferase gene), wherein the reporter gene and the selectable marker gene are operably linked to a promoter (such as a lac promoter); and a multiple cloning site. Optionally, the vectors of the subject invention can further comprise a SLIP sequence, a plurality of thymidine nucleotides that allows for all three frames of any cloned cDNA to be fused to the reporter gene, thereby increasing the efficiency of cloning cDNAs for secreted or membrane-bound proteins.

The invention also relates to a method for cloning novel members of a gene family using plasmid vectors of the present invention. The method includes providing a vector of the subject invention. Preferably, the vector is linearized. The vector can be linearized, for example, with one or more restriction enzymes in order to produce a "sticky end" for ligation to a candidate nucleic acid sequence encoding a potential secreted or membrane-bound protein. The vector comprises DNA encoding a reporter gene lacking a functional signal sequence. The method further includes cutting the candidate nucleic acid sequence with one or more restriction enzymes in order to produce a compatible "sticky end" for ligation to the linearized vector and ligating the candidate nucleic acid sequence to the linearized vector, thereby forming a ligation product. Bacterial cells can then be transformed with the ligation product and colonies can be selected based on expression of the reporter gene functionally linked to the gene encoding the secreted or membrane-bound protein. The method can further include determining the nucleic acid sequence within the transformants from the selected colonies and determining the amino acid sequence based on the nucleic acid sequence.

The present inventors have developed a novel strategy for cloning cDNAs encoding any secreted or membrane-bound proteins based on the use of a plasmid that contains a reporter gene lacking a functional signal sequence. Preferably, the reporter gene is a β-lactamase gene in which the start and signal peptide codons have been deleted. Resistance to β-lactam antibiotics (e.g., ampicillin) can be achieved after the introduction of an in-frame signal peptide sequence from a directionally cloned cDNA. This selection system, termed "Amptrap", efficiently selects mRNAs with intact 5' regions and can be used in conjunction with a degenerate 5'-RACE strategy that requires knowledge of only a single target motif corresponding to as few as three amino acids. Amptrap has been validated in a number of systems and has proven to be highly efficient in the recovery of orthologs of known immune receptors as well as novel forms of immune-related genes. An unusual secreted gene product from a protochordate in which the N terminus consists of two immunoglobulin (Ig) variable (V) domains and the C terminus is a chitin-binding domain has been identified and characterized. Consideration of such molecules is important in discerning the genetic mechanisms that have diversified both innate and adaptive receptors.

The methods and vectors of the subject invention can be utilized for cloning cDNAs encoding any secreted or membrane-bound proteins from a vast array of eukaryotic organisms, including vertebrates and invertebrates. For example, the methods and vectors of the subject invention can be utilized to identify secreted or membrane-bound proteins of reptiles, birds, fish, amphibians, and mammals, such as rodents and humans. The methods and vectors of the subject invention are suitable in a number of potential applications, particularly those that are normally hampered by knowledge of only minimal structural interrelatedness and/or by low concentrations of mRNA that would not be represented in standard EST (expressed sequence tag) libraries.

The methods of the subject invention can be carried out using a plasmid vector comprising a reporter gene lacking a functional signal sequence. For example, the reporter gene can encode a β-lactamase enzyme in which the N-terminal signal peptide has been deleted. The absence of this region precludes the secretion of β-lactamase and results in sensitivity to β-lactam antibiotics (e.g., ampicillin). Secretion of β-lactamase is restored if a cDNA sequence that is inserted 5' and in-frame to the β-lactamase coding sequence encodes both a methionine start codon (ATG) and a signal peptide immediately downstream from the start codon. Advantageously, the cloning of cDNAs that encode intracellular proteins, nuclear proteins, or any other sequence that does not encode a signal peptide, can be selectively eliminated by growth in a selective medium (a β-lactam antibiotic, such as ampicillin). Such irrelevant sequences can drastically reduce the efficiency of recovery of target clones in degenerate, low stringency PCR amplifications.

A selective, directed cloning strategy, which represents a method of the subject invention, and requires only minimal a priori sequence information, is shown in FIG. 1. In the first step, cDNA is synthesized. Chemical synthesis of nucleic acid sequences can be accomplished using methods well known in the art, such as those set forth by Engels et al., *Angew. Chem. Intl. Ed.*, 28:716–734 (1989), CLONTECH's SMART cDNA synthesis manual (www.clontech.com), and Wells et al. *Gene,* 34:315 (1985), the disclosures of which are hereby incorporated by reference. These methods include the phosphotriester, phosphoramidite and H-phosphonate methods of nucleic acid sequence synthesis. Large nucleic acid sequences, for example those larger than about 100 nucleotides in length, can be synthesized as several fragments and ligated together. A preferred method is polymer-supported synthesis using standard phosphoramidite chemistry. The SMART system (CLONTECH) is based on the non-templated addition of polyC to nascent cDNA by reverse transcriptase. The double-stranded cDNA sequences that are produced contain a common, specific anchor sequence at their 5' ends. Using the SMART system, a 5'-RACE PCR reaction is performed in which the specific (SMART) anchor sequence also serves as the 5' primer-binding site and is coupled with a 3' degenerate antisense primer that complements a short region of predicted amino acid sequence identity. Following PCR amplification, amplicons can be cloned directionally into the vector using one or more restriction enzymes. For example, asymmetric Sfi I sites can be utilized. SfiI enzymes are type II restriction endonucleases having two binding surfaces which act cooperatively to grasp two copies of its 13 base pair recognition sequence, 5'-GGCCnnnn↓nGGCC (SEQ ID NO. 6). Only those clones that contain a start codon and signal sequence, fused in-frame to the codons complemented by the 3' PCR primer, will grow on the β-lactam antibiotic. In many applications, the approximate distance between a single conserved priming site and the N-terminal signal peptide can be predicted, thus permitting size selection and further elimination of irrelevant amplicons. PCR amplicons in the range of ~200→800 base pairs (bp) have been cloned and selected successfully using the methods of the subject invention.

Conventional cDNA cloning vectors allow a cDNA sequence to be propagated in a host cell, usually a bacterium or yeast, after insertion of the cDNA into a plasmid at a specific site. Modern vectors allow sequencing of the cDNA inserts by placing primer binding sites both 5' and 3' to the inserted DNA. Subsets of these vectors are also designed for other specific purposes, such as expression of the inserted cDNA sequence in either bacterial or eukaryotic cells by the addition of promoter sequences 5' to the insert. Although these vectors have allowed investigators to clone a large variety of novel sequences from almost any organism, most common, commercially available vectors do not provide a means of selection for the biochemical function of the proteins encoded by inserted cDNA. Because of this condition, searches for transcripts encoding proteins with specific functions or properties can become cumbersome due to the large number of extraneous insertion events that must be screened in order to isolate rare clones of interest. Selection for biochemical functions of the inserted sequences can be valuable in an experiment designed to identify cDNA sequences encoding proteins with a specific biochemical property, such as kinases, DNA-binding proteins, or membrane-bound receptors.

The inventors have designed a new vector system, the Amptrap, which allows rapid and robust selection for cDNA sequences encoding proteins that are secreted or bound to lipid membranes. Using this system, an investigator can rapidly narrow a large pool of cDNA inserts to only those sequences that encode such proteins, while excluding any sequences that encode cytoplasmic proteins, nuclear proteins, or incomplete membrane protein segments. Because the system is based on selection rather than simple screening, clones encoding irrelevant proteins are deleted from the experiment and do not appear in the pool of colonies for analysis, reducing the risk of false positives. All cDNA sequences isolated using this method must contain a methionine start codon in addition to a secretion signal sequence, eliminating isolation of 5'-truncated cDNA sequences. The vector set can accommodate cDNA library construction, either in plasmids or lambda phage.

The Amptrap vectors described in this disclosure, G7311 (FIG. 2) and G7637 (FIG. 3), are plasmids designed to allow direct, robust selection for cDNA sequences that encode secreted or membrane-bound proteins. Both vectors contain a sequence encoding a mature β-lactamase enzyme that lacks a sequence of twenty-three largely hydrophobic amino acids at the N-terminus of the protein, the signal peptide, that directs export of the wildtype protein into the bacterial periplasmic space. Without this signal peptide, β-lactamase cannot be secreted and remains within the bacterial cell.

Because the β-lactamase enzyme must be secreted into the periplasmic space of the bacterium in order to confer resistance to β-lactam antibiotics such as ampicillin, a bacterium bearing G7311 or G7637 is ampicillin-sensitive. However, if a cDNA sequence inserted 5' to the β-lactamase sequence contains both a methionine start codon (ATG) and codons for a signal peptide immediately 3' to the initiation sequence that can be fused in frame to the β-lactamase coding sequence, secretion of β-lactamase is restored and the host clone will express ampicillin resistance. If the cDNA fails in either of these two requirements, the bacterium will remain ampicillin-sensitive and the clone will not be propagated upon selection.

The G7637 vector is similar to the G7311 vector, except for the addition of a sequence of 13 thymidine residues at the 5' region of the β-lactamase coding region (the "SLIP" sequence: CLONTECH). This region allows slippage of the transcription and translation machinery of the cell such that peptides encoded by all three frames of any cDNA become fused to β-lactamase, thus removing the requirement for proper in-frame fusion of an open reading frame in the cDNA to the β-lactamase sequence, and increasing the efficiency of selection for signal sequences.

Figure 4A:
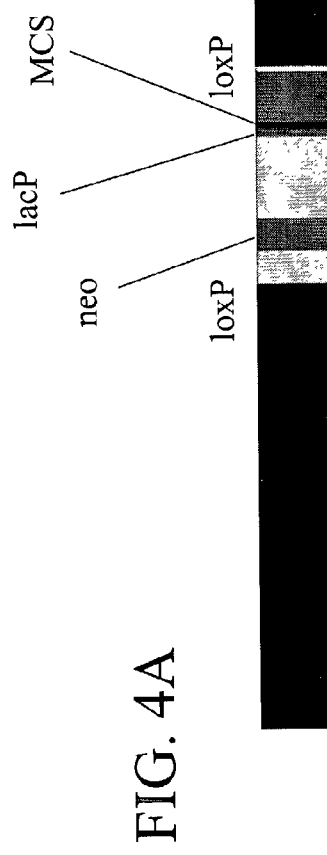
FIGS. 4A and 4B are maps of the phage vectors λ7311 and λ7637, respectively, of the present invention.
Figure 4B:
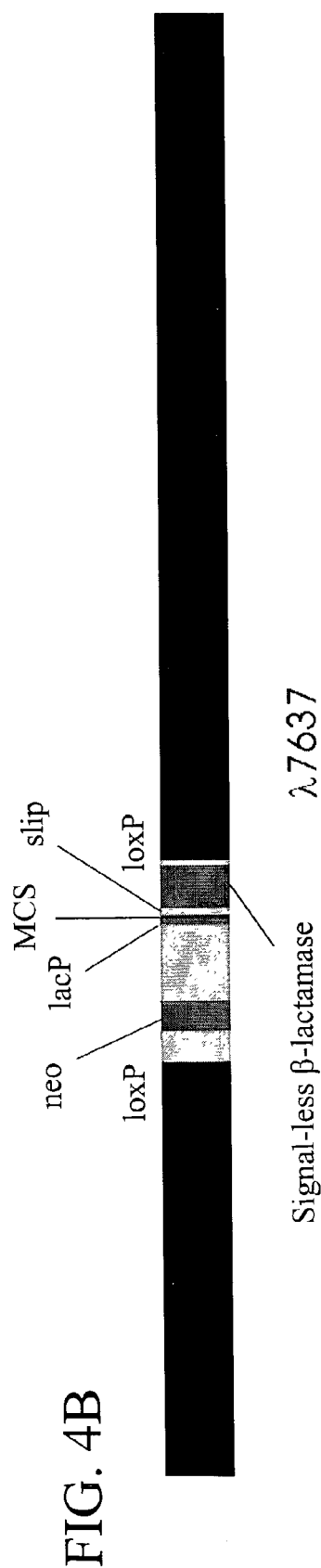

In order to facilitate construction of large cDNA libraries, the plasmid vectors G7311 and G7637 have been inserted into phage lambda-based vectors to form λ7311 (FIG. 4A) and λ7637 (FIG. 4B). Derived from CLONTECH's λTripleX (www.clontech.com), the λ7311 and λ7637 phage vectors contain loxP recombination sequences that allow in vivo plasmid excision.

In addition to the disclosed vectors, the inventors have designed a strategy for the cloning of novel members of a gene family using the plasmid vectors. A strategy using the plasmid vector G7311 is shown in FIG. 1. In this system, cDNA is synthesized using CLONTECH's SMART system (CLONTECH, 1020 East Meadow Circle, Palo Alto, Calif. 94303-4230, USA, available at www.clontech.com/smart/), which produces double-stranded cDNA sequences containing a common, specific anchor sequence at their 5' ends. This anchor sequence is used as a 5' primer binding site in a PCR reaction, coupled with a 3' degenerate antisense primer based on amino acids thought to be conserved throughout a given gene family. By performing PCR, directionally cloning the amplicons into the G7311 vector, and then selecting on ampicillin, only those sequences that contain a start codon and signal sequence, fused in frame to the codons dictated by the 3' PCR primer, will be propagated in bacterial colonies. Other 5'RACE primers can also be utilized in the present invention. If domains of a particular size are expected from the PCR amplification, size selection can be used to screen out clones that depart from the expected insert size.

SMART stands for Switch Mechanism At 5' end of the RNA Transcript. SMART cDNA synthesis begins with just nanograms of either total or poly $A^+$ RNA. A modified oligo(dT) primer is used to prime the first-strand reaction. When reverse transcriptase (RT) reaches the 5' end of the mRNA, the enzyme's terminal transferase activity adds a few deoxycytidine (dC) nucleotides. The 3' end of the SMART oligonucleotide anneals with the (dC) stretch, forming an extended template. RT then switches templates and replicates the oligonucleotide. The resulting single-stranded (ss) cDNA contains the complete 5' end of the mRNA template, as well as the sequence complementary to the SMART oligonucleotide, called the SMART anchor. This anchor, together with the modified oligo(dT) sequence, serves as a universal priming site for long-distance (LD) PCR, primer extension, or RACE amplification.

All steps in this method provide very strong tools for the elimination of undesirable or artifactual sequences. Using this system, primers corresponding to motifs containing as few as two known amino acids have produced successful amplification and targeted cloning of a cDNA sequence encoding major histocompatibility complex class II, a member of a specific family of membrane-bound proteins. Thus, because of the relaxed requirements for degenerate priming sites, this strategy allows amplification and cloning of novel gene family members based on only very limited knowledge of conserved motifs.

The PCR strategy described above, while applicable to other signal trap vectors, allows a very easy and robust way to clone sequences using the SfiI sites in the Amptrap. SfiI is a very rare cutter in DNA, cutting once every 65,536 bases in theory, and also leaves unique ends after cutting because it has a "separated" recognition site (5'-GGCCNNNN^NG-GCC (SEQ ID NO. 6)). Therefore, the inventors' SfiI-containing vector coupled with the inventors' PCR method is the most powerful approach to clone secreted/membrane proteins with short, specific amino acid motifs. Other restriction enzymes that provide for incorporation of inserts into the vector, including directional cloning of inserts, can also be used in the present invention.

Amptrap-based selection for cDNAs allows cloning and selection to occur in bacterial cells, which are very amenable to DNA transformation and propagation, and are preferable to yeast in many experiments. Because the mechanism of the Amptrap system can operate by antibiotic resistance rather than color change from alkaline phosphatase activity during colony formation (as described by Chen and Leder *Nucleic Acids Res.* 27: 1219–22 (1999) and Lee, et al. *J. Bacteriol.* 181: 5790–99(1999)), screens for secreted/membrane proteins using Amptrap are more convenient and potentially more robust, as only those colonies containing signal-positive cDNA inserts will survive in the selection. The requirement for subjective determination of color changes using the alkaline phosphatase system is eliminated.

The vectors of the subject invention can carry a constitutively expressed neomycin phosphotransferase gene, which confers resistance to antibiotics such as kanamycin and neomycin, thus allowing selection of $Kan^R$-$Amp^R$ doubly resistant clones, as described in the Examples section. Advantageously, if an inserted ORF contains a methionine start codon coupled to a signal peptide that is in frame with the β-lactamase ORF, secretion of β-lactamase is restored and transformed bacterial clones acquire a $Kan^R$ $Amp^R$ doubly resistant phenotype, allowing their direct selection on Kan+Amp medium.

The subject invention is exemplified by using *Escherichia coli* strain DH10B as the cloning host. However, any prokaryotic cell (including other *E. coli* strains) capable of accommodating recombinant DNA propagation without rearrangement could be used in the present invention.

The utility of the methods and vectors of the subject invention can be expanded to include cloning directed at antigenic epitopes for which an amino acid sequence can be inferred. This technique would extend to include antigens present on novel infectious agents, tumor-specific antigens, and other structures that are not necessarily encoded in known genomes and other structures that are not necessarily encoded in known genomes. For example, cDNA from cells infected with a virus that is novel but related antigenically to other, previously characterized viruses could be isolated and prepared for Amptrap cloning. Degenerate primers designed to amplify conserved sequences from the novel virus could be produced after analysis of protein sequences from the other, known members of its family. If amplicons can be generated successfully from the cDNA of the novel virus, they would provide immediate molecular probes for the cloning of its entire genome, thus aiding in the eventual isolation of the pathogen. Alternatively, analysis of Amptrap libraries from various tumors or tumor cell lines could provide a survey of secreted or membrane-bound protein sequences in cancerous tissues, thus aiding in searches for antigens or other factors expressed specifically or at high levels in certain tumors. Such antigens may be attractive therapeutic targets.

Recombinant DNA techniques used herein are generally set forth in Sambrook et al., Molecular Cloning: A Laboratory Manual, Cold Spring Harbor Laboratory Press, Cold Spring Harbor, N.Y., (1989); by Ausubel et al., eds Current Protocols in Molecular Biology, Current Protocols Press, (1994); and by Berger and Kimmel, Methods in Enzymology: Guide to Molecular Cloning Techniques, Vol. 152, Academic Press, Inc., San Diego, Calif., (1987), the disclosures of which are hereby incorporated by reference. For example, nucleic acids and/or vectors can be introduced into host cells by well-known methods, such as, calcium phosphate transfection, DEAE-dextran mediated transfection, transfection, microinjection, cationic lipid-mediated transfection, electroporation, transduction, scrape loading, ballistic introduction and infection. Preferably, according to the methods of the subject invention, the host cells are transformed with nucleic acids and/or vectors via electroporation.

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman [1988] *Proc. Natl. Acad. Sci. USA* 85(8):2444–2448; Altschul et al. [1990] *J. Mol. Biol.* 215 (3):403–410; Thompson et al. [1994] *Nucleic Acids Res.* 22(2):4673–4680; Higgins et al. [1996] *Methods Enzymol.* 266:383–402; Altschul et al. [1990] *J. Mol. Biol.* 215(3): 403–410; Altschul et al. [1993] *Nature Genetics* 3:266–272).

Various restriction enzymes can be used to cleave or cut nucleic acids according to the methods of the subject invention. Preferably, type II restriction endonucleases are utilized. For example, endonucleases such as EcoRI, BamHI, HindIII, XhoI, NotI, SacI, SacII, and SalI can be utilized. More preferably, the SfiI endonuclease is utilized according to the methods of the present invention.

As used herein, the term "secreted protein" refers to a polypeptide that is extruded from the cell through the cell membrane. Secreted proteins include, but are not limited to, those polypeptides containing a signal sequence that are directed into the endoplasmic reticulum, or other organelles and subsequently directed out of the cell through a vesicle. Many secreted proteins, such as cytokines and hormones, are of therapeutic importance.

As used herein, the term "membrane-bound protein" refers to a polypeptide that is directed to a membrane-bound organelle and/or the cell membrane, and is not immediately secreted from the cell but remains associated with the membrane for a time. Therefore, membrane-bound proteins are inclusive of external membrane proteins (which are entirely outside of the cell membrane but bound to it by weak molecular attractions, such as ionic, hydrogen, and/or Van der Waals forces) and intrinsic membrane proteins that are embedded in the membrane. Membrane-bound proteins include, for example, integral membrane proteins, transmembrane proteins (which are amphipathic, having hydrophobic and hydrophilic regions and, therefore, having one or more membrane-spanning domains, such as type I and type II transmembrane proteins and multipass transmembrane receptors), peripheral membrane proteins, and lipid-anchored proteins. Many membrane-bound proteins are glycoproteins. Many membrane-bound proteins are receptors, such as the epidermal growth factor (EGF) receptor and G protein (guanine nucleotide binding proteins) coupled receptors.

As used herein, the term "reporter gene" refers to a nucleic acid sequence encoding a gene product (reporter molecule) that allows the presence of a vector (carrying a foreign nucleic acid sequence, such as a foreign gene) to be identified in eukaryotic or prokaryotic cells. Examples include the amp (ampicillin resistance) gene, β-lactamase, and genes encoding a chromogenic molecule, such as BCIP (5-bromo-4-chloro-3-indooylphosphate) or alkaline phosphatase. Only cells carrying the reporter gene can grow in the presence of the appropriate drug (the antibiotics neomycin and ampicillin, for example). Preferably, the reporter gene is one in which the reporter molecule encoded by the reporter gene must be secreted outside of the cell in order to operate. Any reporter gene that would allow signal sequence rescue by selection can be utilized.

As used herein, the term "selectable marker gene" refers to a nucleic acid sequence encoding a gene product (selectable marker molecule) that can be utilized to detect initial transformants. Therefore, the selectable marker gene can be constitutively expressed by a promoter sequence within the vector construct. Preferably, the selectable marker gene can be expressed independently from the reporter gene. More preferably, the reporter gene is operably linked to a first promoter sequence and the selectable marker gene is operably linked to a second (separate) promoter sequence. Examples of selectable marker genes include a neomycin-resistance gene (such as neomycin phosphotransferase), tetracycline-resistance gene, chloramphenicol-resistance gene (such as chloramphenicol acetyl transferase (CAT)), and bleomycin-resistance gene.

As used herein, the term "operably linked" refers to the functional and positional relationship between a nucleic acid sequence and a regulatory sequence. Polynucleotide sequences may be "operably linked" to regulatory sequences such as promoters and enhancers. A nucleic acid is "operably linked" when it is placed into a functional relationship with another nucleic acid sequence. For example, DNA for a presequence or secretory leader is "operably linked" to DNA encoding a polypeptide if it is expressed as a preprotein that participates in the secretion of the polypeptide; a promoter or enhancer is "operably linked" to a coding sequence if it affects the transcription of the sequence; or a ribosome binding site is "operably linked" to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers can be used in accordance with conventional practice.

As used herein, the terms "signal sequence", "leader sequence", or "signal peptide", refer to a sequence (e.g., about 7 to about 20 residues) added to the amino-terminal end of a polypeptide chain that forms an amphipathic helix allowing the nascent polypeptide to migrate in or through cellular membranes such as the endoplasmic reticulum or the cell membrane. The signal sequence is generally cleaved from the polypeptide after the protein has crossed the membrane. As used herein, the term "signal sequence" may be used generically to refer to the signal peptide on a polypeptide chain, or to the nucleotides encoding the signal peptide.

As used herein, the term "sequencing" refers to the determination of the order of the repeating units in a nucleic acid sequence (the nucleotides in a DNA molecule) or a polypeptide sequence (the amino acids of a protein). For example, in the case of DNA, copies of the DNA to be sequenced can be made and labeled with fluorescent markers before they are identified using a sequencing machine. For proteins, single amino acid residues can be removed from one end of the protein and identified one at a time using an automated system.

The terms "comprising", "consisting of", and "consisting essentially of" are defined according to their standard meaning and may be substituted for one another throughout the instant application in order to attach the specific meaning associated with each term.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Figure 2:
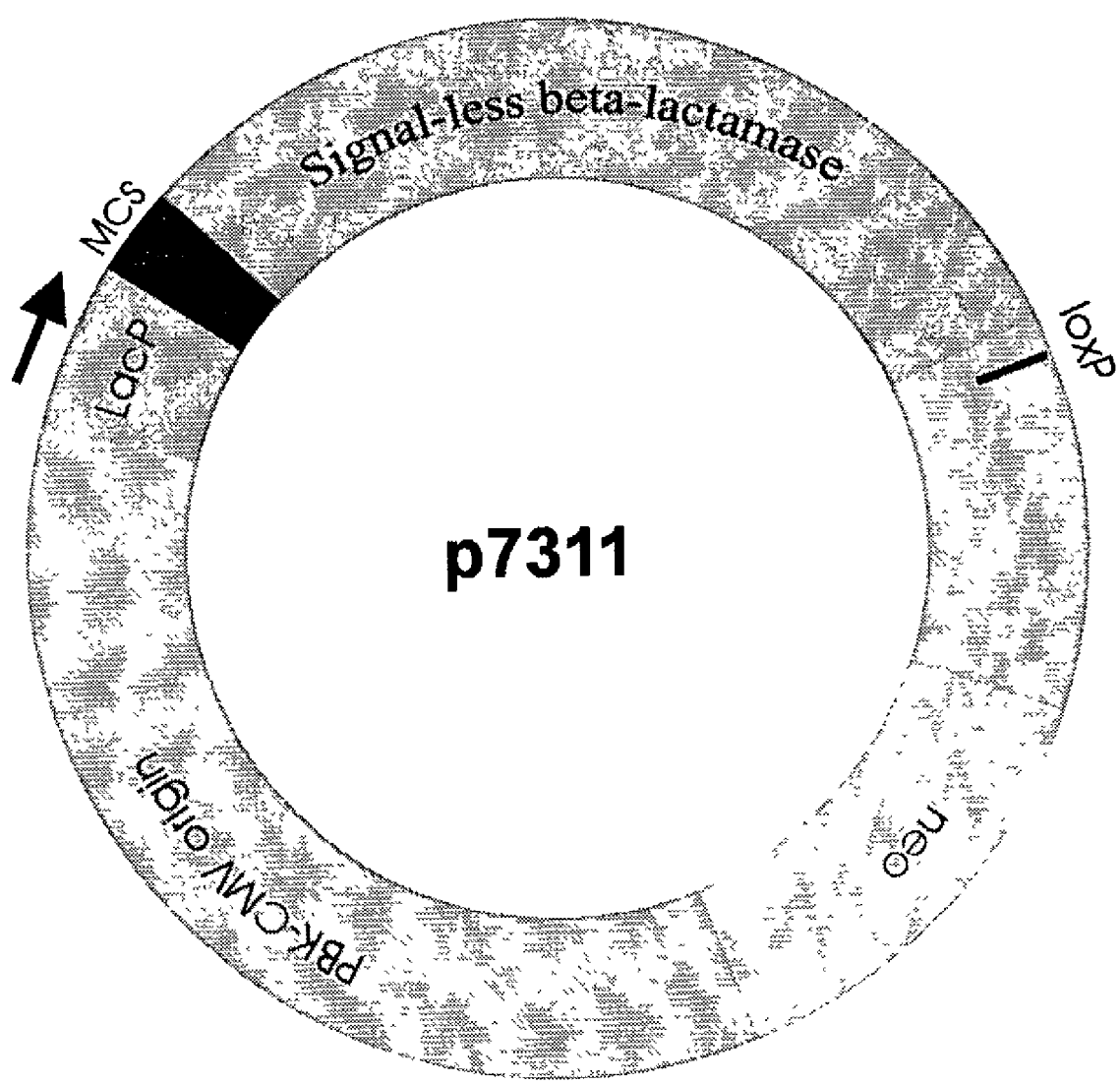
FIG. 2 is a map of the Amptrap vector G7311 of the present invention.
Figure 3:
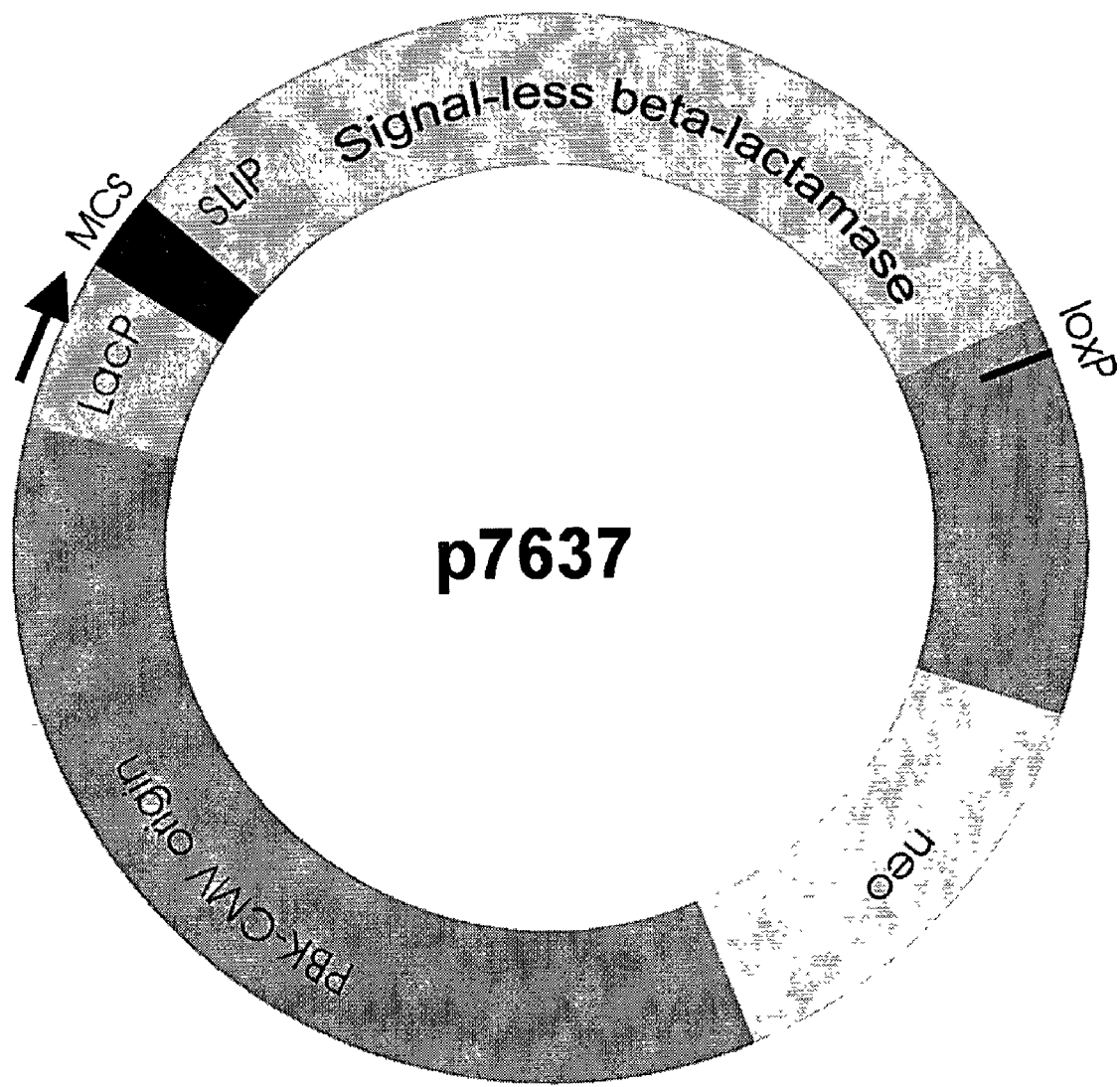
FIG. 3 is a map of the Amptrap vector G7637 of the present invention.

Amplification of cDNAs Encoding Secreted or Membrane-Bound Proteins Containing Specific Amino Acid Motifs In order to select cDNAs that encode secreted or membrane-bound proteins, the cloning vector G7311 (referred to herein as an "Amptrap" vector) was designed by the present inventors, which allows selection for signal sequence-encoding regions by β-lactamase rescue (as shown in FIG. 2). The Amptrap vector shown contains a 5'-truncated β-lactamase gene driven by a Lac promoter. The product of the modified β-lactamase gene lacks the signal peptide present in the wild-type protein and is therefore unable to be exported into the bacterial periplasmic space. An asymmetric pair of SfiI sites for insertion of cDNA lies immediately 5' to the β-lactamase open reading frame (ORF). A separate neomycin phosphotransferase marker was included to allow propagation of the vector without cDNA inserts. Because β-lactamase must be secreted into the periplasmic space to produce ampicillin resistance, bacterial cells bearing an unmodified Amptrap plasmid display a kanamycin-resistant, ampicillin-sensitive ($Kan^R$ $Amp^S$) antibiotic resistance phenotype. To select for signal peptide-encoding cDNAs, cDNA sequences can be cloned directionally into the Amptrap vector at its asymmetric SfiI sites, creating a fusion transcript between the inserted cDNA and the β-lactamase gene. If an inserted ORF contains a methionine start codon coupled to a signal peptide that is in frame with the β-lactamase ORF, secretion of β-lactamase is restored and transformed bacterial clones acquire a $Kan^R$ $AmP^R$ doubly resistant phenotype, allowing their direct selection on Kan+Amp medium.

In order to increase specificity in cloning using the Amptrap vector, the inventors adopted a single short-primer PCR strategy for amplification of novel gene family members. In this technique, PCR amplification of cDNA is performed using a 5'-RACE primer coupled with a degenerate 3' antisense primer, representing between three and five residues of a conserved amino acid motif in a given family of proteins. An anchor sequence containing an SfiI site is coupled to the 3' degenerate sequence for subsequent cloning. The spacing between the degenerate codons and the SfiI site in the 3' primer was designed so that rescue of β-lactamase secretion would require translation of the degenerate sequence in the desired frame upon cloning and expression in the Amptrap vector. Various primer sets were used to amplify subsets of cDNA sequences containing the 5' regions of cDNAs plus potential coding sequence, all of which ended in the primer-encoded amino acid motifs.

EXAMPLE 2

Cloning of Expressed Sequence Tags (EST) Sequences Using the Amptrap Vector cDNA was synthesized from Florida lancelet (*Branchiostoma floridae*) and sea lamprey (*Petromyzon marinus*) tissues and cloned into an Amptrap vector. 57 sequences were analyzed by BLASTX searching of the Genbank database. Although 17 sequences failed to match known sequences in Genbank, all of the remaining 40 sequences were found to encode proteins that are likely to be secreted or bound to membranes (Table 1).

TABLE 1

Beta-lactamase fusion ("amptrap") EST sequences

| G# | Tissue | Source | Stock? | Gel date | Comments |
|---|---|---|---|---|---|
| 7024 | PMP | 20000827, clone 3 | Y | 20000928 | no match* |
| 7026 | PMI | 20000827, clone 5 | Y | 20000830 | trypsinogen b1† |
| 7027 | PMI | 20000827, clone 6 | Y | 20000830 | no match* |
| 7031 | PMI | 20000827, clone 10 | Y | 20000830 | trypsinogen b1† |
| 7033 | PMI | 20000827, clone 12 | Y | 20000830 | trypsinogen b1† |
| 7034 | PMI | 20000827, clone 13 | Y | 20000905 | trypsinogen b1† |
| 7035 | PMI | 20000827, clone 14 | Y | 20000905 | chymotrypsinogen† |
| 7037 | PMI | 20000827, clone 16 | Y | 20000905 | trypsinogen† |
| 7038 | PMI | 20000827, clone 17 | Y | 20000905 | trypsinogen† |
| 7039 | PMI | 20000827, clone 18 | Y | 20000928 | no match* |
| 7046 | PMP | 20000831, clone 3 | Y | 20000905 | no match* |
| 7047 | PMI | 20000831, clone 19 | Y | 20000905 | trypsinogen† |
| 7048 | PMI | 20000831, clone 21 | Y | 20000905 | no match* |
| 7049 | PMI | 20000831, clone 29 | Y | 20000905 | chymotrypsinogen† |
| 7212 | PMI + PMP | 20000915, clone 1 | Y | 20000928 | elastase† |
| 7213 | PMI + PMP | 20000915, clone 2 | Y | 20000928 | chymotrypsin-like† |
| 7214 | PMI + PMP | 20000915, clone 3 | Y | 20000928 | no match* |
| 7215 | PMI + PMP | 20000915, clone 4 | Y | 20000928 | cytochrome C oxidase† |
| 7216 | PMI + PMP | 20000915, clone 5 | Y | 20000928 | defender against cell death-1 (DAD-1)† |
| 7535 | PMI + PMP | array, plate 3, C1 | Y | 20001120 | no match* |
| 7536 | PMI + PMP | array, plate 3, D1 | Y | 20001120 | trypsinogen† |
| 7537 | PMI + PMP | array, plate 3, E1 | Y | 20001120 | no match* |
| 7538 | PMI + PMP | array, plate 3, F1 | Y | 20001120 | no match* |
| 7541 | PMI + PMP | array, plate 3, A2 | Y | | trypsinogen† |
| 7542 | PMI + PMP | array, plate 3, B2 | Y | | procolipase† |
| 7543 | PMI + PMP | array, plate 3, C2 | Y | | trypsinogen† |
| 7544 | PMI + PMP | array, plate 3, D2 | Y | | trypsinogen† |
| 7545 | PMI + PMP | array, plate 3, E2 | Y | | trypsinogen† |
| 7546 | PMI + PMP | array, plate 3, F2 | Y | | trypsinogen† |
| 7547 | PMI + PMP | array, plate 3, G2 | Y | | trypsinogen† |
| 7548 | PMI + PMP | array, plate 3, H2 | Y | | trypsinogen† |
| 7676 | PMI + PMP | array, plate 3, F6 | Y | 20001213 | trypsinogen a† |
| 7677 | PMI + PMP | array, plate 3, H6 | Y | 20001213 | no match* |
| 7679 | PMI + PMP | array, plate 3, D8 | Y | 20001213 | trypsinogen a† |
| 7681 | PMI + PMP | array, plate 3, H8 | Y | 20001213 | trypsinogen b† |
| 7682 | PMI + PMP | array, plate 3, A9 | Y | 20001213 | trypsinogen a† |
| 7683 | PMI + PMP | array, plate 3, B9 | Y | 20001213 | trypsinogen a† |
| 7684 | PMI + PMP | array, plate 3, C9 | Y | 20001213 | trypsinogen b† |
| 7685 | PMI + PMP | array, plate 3, G9 | Y | 20001213 | trypsinogen b† |
| 7686 | PMI + PMP | array, plate 3, H9 | Y | 20001213 | trypsinogen b† |
| 7687 | PMI + PMP | array, plate 3, A10 | Y | 20001213 | trypsinogen b† |
| 7688 | PMI + PMP | array, plate 3, E10 | Y | 20001213 | no match* |
| 7689 | PMI + PMP | array, plate 3, G10 | Y | 20001213 | trypsinogen b† |
| 7690 | PMI + PMP | array, plate 3, A11 | Y | 20001213 | trypsinogen b† |
| 7691 | PMI + PMP | array, plate 3, F11 | Y | 20001213 | trypsinogen b† |
| 7692 | PMI + PMP | array, plate 3, G11 | Y | 20001213 | no match* |
| 7694 | PMI + PMP | array, plate 3, C12 | Y | 20001213 | trypsinogen b† |
| 7695 | PMI + PMP | array, plate 3, D12 | Y | 20001213 | trypsinogen b† |
| 7696 | PMI + PMP | array, plate 3, F12 | Y | 20001213 | trypsinogen b† |
| 7748 | BFD | pilot ligations, G7637 | N | 20001222 | cytochrome C oxidase subunit III† |
| 7750 | BFD | pilot ligations, G7637 | N | 20001222 | no match* |
| 7752 | BFD | pilot ligations, G7637 | N | 20001222 | no match* |
| 7754 | BFD | pilot ligations, G7637 | N | 20001222 | calsequestrin 1† |
| 7756 | BFD | pilot ligations, G7637 | N | 20001222 | no match* |
| 7758 | BFD | pilot ligations, G7637 | N | 20001222 | NADH dehydrogenase subunit 4L† |
| 7760 | BFD | pilot ligations, G7637 | N | 20001222 | no match* |
| 7762 | BFD | pilot ligations, G7637 | N | 20001222 | no match* |

*No matches after BLASTX search of Genbank
†Membrane protein
‡Artifact (intracellular protein or 3' UTR of cDNA))
BFD Branchiostoma floridae pooled dorsal regions
PMI Petromyzon marinus intestine
PMP Petromyzon marinus protovertebral arch

EXAMPLE 3

Amplification of Candidate Immune-Type Receptor Genes from *Branchiostoma floridae, Raja eglanteria*, and *Petromyzon marinus*

In order to identify potential new members of the novel immune-type receptor (NITR) gene family previously described in teleost fish, cDNA sequences from Florida lancelet *Branchiostoma floridae*, clearnose skate *Raja eglanteria*, and sea lamprey *Petromyzon marinus* tissues were amplified by 5'-RACE PCR using various 3' primers and the 5'-SMART oligonucleotide. These primers included:

```
nitrVYWFR-Sfi:  5'TGGCCGAGGCGGCCCNCGRAACCARTANAC-3';   (SEQ ID NO. 8)

nitrVYWF-Sfi:   5'GACTGGCCGAGGCGGCCCRAACCARTANAC-3';   (SEQ ID NO. 9)

nitrYWFR-Sfi:   5'-GACTGGCCGAGGCGGCCCNCGRAACCARTA-3';  (SEQ ID NO. 10)

nitrYWFK-Sfi:   5'-GACTGGCCGAGGCGGCCCYTTRAACCARTA-3';  (SEQ ID NO. 11)

nitrWFR1-Sfi:   5'-GACTGGCCGAGGCGGCCCNCGRAACCA-3';     (SEQ ID NO. 12)

nitrWFR2-Sfi:   5'-GACTGGCCGAGGCGGCCCYCTRAACCA-3'; and (SEQ ID NO. 13)

nitrWFK-Sfi:    5'GACTGGCCGAGGCGGCCCYTTRAACCA-3'.     (SEQ ID NO. 14)
```

The pool of amplicons were subsequently cloned into the Amptrap vector. After sequence analysis of 222 amplicons, 148 amplicons were found to encode secreted or membrane-bound proteins, 19 amplicons encoded artifactual sequences (ORFs for intracellular proteins or 3' untranslated regions of cDNAs), and 55 amplicons failed to match any known sequences in Genbank (available at www.ncbi.nlm.nih.gov) after BLASTX searching. 41 of the 222 amplicons encoded candidate immunoglobulin-superfamily domains, which were the targets of the screen (Table 2).

TABLE 2

Beta-lactamase fusion ("Amptrap") PCR-directed sequences

| G# | Target (primer) | Tissue | Comments |
|---|---|---|---|
| 7950 | NITR (pool of 7) | OM | integral membrane protein 2B† |
| 7951 | | OM | immunoglobulin superfamily molecule† |
| 7952 | | OM | immunoglobulin superfamily molecule† |
| 7953 | | OM | tetraspan protein family (TM4SF)† |
| 7954 | | OM | immunoglobulin superfamily molecule (2)† |
| 7955 | | OM | immunoglobulin superfamily molecule† |
| 7956 | | OM | immunoglobulin superfamily molecule† |
| 7957 | | OM | immunoglobulin superfamily molecule† |
| 7958 | | OM | immunoglobulin superfamily molecule† |
| 7961 | | DR | No Match* |
| 7962 | | DR | No Match* |
| 7963 | | DR | claudin† |
| 7964 | | DR | claudin† |
| 7965 | | DR | claudin† |
| 7966 | | DR | claudin† |
| 7967 | | DR | claudin† |
| 7968 | | DR | lipid kinase (?)† |
| 7969 | | DR | claudin† |
| 7971 | | DR | claudin† |
| 7976 | | BFV | NADH dehydrogenase† |
| 7977 | | BFV | IgSF domain† |
| 8020 | NITR (pool of 7) | Reg | transmembrane protein, PIGPC1† |
| 8021 | | Reg | transmembrane protein, PIGPC1† |
| 8022 | | Reg | transmembrane protein, PIGPC1† |
| 8023 | | Reg | transmembrane protein, PiGPC1† |
| 8024 | | Reg | Immunoglobulin light chain II/III† |
| 8025 | | Reg | transmembrane protein, PIGPC1† |
| 8026 | | Reg | 3' UTR‡ |
| 8028 | | Reg | immunoglobulin superfamily molecule† |
| 8031 | | Reg | Candidate immunoglobulin superfamily molecule† |
| 8032 | | Reg | transmembrane protein, PIGPC1† |
| 8033 | | Reg | Candidate immunoglobulin superfamily molecule† |
| 8034 | | XL | Golgi membrane protein p18† |
| 8036 | | XL | MHC Class II† |
| 8037 | | XL | MHC Class II† |
| 8038 | | XL | immunoglobulin light chain† |
| 8039 | | XL | immunoglobulin light chain† |
| 8052 | CD3 (YQPL) | BFV | α-amylase† |
| 8053 | | BFV | α-amylase† |
| 8054 | | BFV | α-amylase† |
| 8055 | | BFV | α-amylase† |
| 8150 | NITR (pool of 7) | Reg | candidate Ig domain (distinct from G8152)† |
| 8151 | | Reg | candidate Ig domain (distinct from G8152)† |
| 8152 | | Reg | immunoglobulin superfamily molecule† |
| 8153 | | Reg | candidate Ig domain (distinct from G8152)† |
| 8227 | MHC (CHVEH) | BFV | amphi-lipase† |
| 8293 | NITR (pool of 5) | BFV | No Match* |
| 8294 | | BFV | No Match* |
| 8295 | | BFV | No Match* |
| 8296 | | BFV | No Match* |
| 8297 | | BFV | immunoglobulin superfamily molecule† |
| 8298 | | BFV | No Match* |
| 8309 | NITR (WFR1, WFR2) | BFV | cytochrome C oxidase† |
| 8310 | | BFV | CD81/CD9-like† |
| 8311 | | BFV | No Match* |
| 8312 | | BFV | CD81/CD9-like† |
| 8313 | | BFV | CD81/CD9-like† |
| 8314 | | BFV | cytochrome B† |

TABLE 2-continued

Beta-lactamase fusion ("Amptrap") PCR-directed sequences

| G# | Target (primer) | Tissue | Comments |
|---|---|---|---|
| 8315 | | BFV | No Match* |
| 8316 | | BFV | CD81/CD9-like† |
| 8317 | | BFV | No Match* |
| 8318 | | BFV | CD81/CD9-like† |
| 8358 | MHC (CXV) | BFV | Cathepsin |
| 8359 | | BFV | Fibropellin III, Notch (?)† |
| 8360 | | BFV | Fibropellin III, Notch (?)† |
| 8361 | | BFV | No Match* |
| 8362 | | BFV | Fibropellin III, Notch (?)† |
| 8363 | | BFV | Notch, SP1070 (D. melanogaster)† |
| 8364 | | BFV | folate receptor† |
| 8365 | MHC (CXVXH2) | BFV | myosin heavy chain, 3' end‡ |
| 8366 | MHC (CXV) | Reg | MHC Class II† |
| 8367 | | Reg | MHC Class II† |
| 8368 | | Reg | No Match* |
| 8369 | | Reg | MHC Class II† |
| 8370 | | Reg | MHC Class II† |
| 8371 | | Reg | MHC Class II† |
| 8372 | | Reg | connective tissue growth factor† |
| 8373 | | Reg | connective tissue growth factor† |
| 8382 | NITR (1–5 OR 6–7) | BFV | No Match* |
| 8383 | | BFV | CD81/CD9-like† |
| 8384 | | BFV | cytochrome C oxidase† |
| 8385 | | BFV | cytochrome C oxidase† |
| 8386 | | BFV | CD81/CD9-like† |
| 8387 | | BFV | cytochrome B† |
| 8388 | | BFV | PDGF-b (?)Δ |
| 8390 | | BFV | CD81/CD9-like† |
| 8391 | | BFV | CD81/CD9-like† |
| 8392 | | BFV | NADH dehydrogenase† |
| 8393 | | BFV | cytochrome B† |
| 8394 | MHC (CXV) | BFV | fibropellin III† |
| 8395 | | BFV | fibropellin III† |
| 8396 | | BFV | No Match* |
| 8397 | | BFV | Notch2† |
| 8398 | | BFV | No Match* |
| 8399 | | BFV | α2-macroglobulin receptor (LDL-related)† |
| 8400 | | BFV | collagen (?)† |
| 8401 | | BFV | asialoglycoprotein receptor† |
| 8402 | | BFV | Cathepsin-like (?)† |
| 8403 | | BFV | fibropellin III† |
| 8404 | | BFV | No Match* |
| 8405 | | BFV | Cathepsin-L-like† |
| 8432 | NITR (1–4 OR 5–7) | PMP | No Match* |
| 8433 | | PMP | Transport protein (?)† |
| 8435 | | PMP | similar to repeat-rich proteins‡ |
| 8436 | | PMP | Repetitive sequence‡ |
| 8437 | | PMP | Repetitive sequence‡ |
| 8438 | | PMP | Repetitive sequence‡ |
| 8439 | | PMP | Collagen† |
| 8444 | | PMP | Repetitive sequence‡ |
| 8445 | | PMP | Repetitive sequence‡ |
| 8456 | MHC (CXV) | PMP | No Match* |
| 8457 | | PMP | No Match* |
| 8458 | | PMP | β-actin‡ |
| 8459 | | PMP | β-actin‡ |
| 8460 | | PMP | lysosomal transporter protein† |
| 8461 | | PMP | lysosomal transporter protein† |
| 8462 | | PMP | lysosomal transporter protein† |
| 8463 | | PMP | lysosomal transporter protein† |
| 8488 | "J" (FGXG) | BFV | short ORF with signal sequence; not Ig-like† |
| 8489 | | BFV | short ORF with signal sequence; not Ig-like† |
| 8490 | | BFV | short ORF with signal sequence; not Ig-like† |
| 8491 | | BFV | short ORF with signal sequence; not Ig-like† |
| 8492 | | BFV | short ORF with signal sequence; not Ig-like† |
| 8493 | | BFV | short ORF with signal sequence; not Ig-like† |
| 8495 | | BFV | possible immunoglobulin superfamily molecule† |
| 8496 | | BFV | short ORF with signal sequence; not Ig-like† |
| 8497 | | BFV | No Match* |
| 8498 | "J" (FGXG) | Reg | ATP synthase F0, subunit 6† |
| 8503 | | Reg | synaptophysin-like (short region of high similarity)† |
| 8505 | | Reg | ATP synthase F0, subunit 6† |
| 8510 | "J" (GXGT) | BFV | No Match* |
| 8511 | | BFV | poly-A‡ |
| 8512 | | BFV | Repetitive sequence? ‡ |
| 8513 | | BFV | "barrier to autointegration" factor‡ |
| 8514 | | BFV | UCC1/ependymin (ECM protein)† |
| 8517 | | BFV | No Match hypothetical H. sapiens gene, F22162_1* |
| 8519 | | BFV | PSSP-94 (secreted protein)† |
| 8520 | | BFV | No Match C. elegans hypothetical protein; "NOV"* |
| 8521 | | BFV | NADH dehydrogenase† |
| 8523 | | BFV | potassium channel† |
| 8527 | | BFV | NADH dehydrogenase† |
| 8528 | | BFV | NADH dehydrogenase† |
| 8529 | | BFV | α-amylase† |
| 8530 | | BFV | No Match* |
| 8531 | | BFV | tetraspanin -- 29Fa; D1-7; CD63† |
| 8532 | | BFV | No Match* |
| 8533 | | BFV | Ca-binding protein† |
| 8538 | IgSF (YXC) | BFV | scavenger receptor† |
| 8539 | | BFV | cytochrome C oxidase† |
| 8540 | | BFV | No Match* |
| 8541 | | BFV | scavenger receptor; zonadhesin† |
| 8542 | | BFV | No Match -- possibly fibropellin* |
| 8543 | | BFV | cytochrome C oxidase† |
| 8544 | | BFV | cytochrome C oxidase† |
| 8545 | | BFV | cytochrome C oxidase† |
| 8546 | | BFV | scavenger receptor† |
| 8547 | | BFV | No Match* |
| 8548 | | BFV | cytochrome C oxidase† |
| 8549 | | BFV | cytochrome C oxidase† |
| 8550 | | BFV | poly-A?‡ |
| 8552 | IgSF (YXC) | Reg | No Match* |
| 8553 | | Reg | No Match* |
| 8555 | "J" GXGT) | Reg | ATP synthase subunit F0† |
| 8557 | | Reg | cytochrome b558α† |
| 8561 | "J" GXGT) | Reg | No Match C. elegans hypothetical protein* |
| 8562 | | Reg | immunoglobulin light chain† |
| 8563 | | Reg | α-interferon-inducible protein - possible signal peptide† |
| 8565 | | Reg | α-interferon-inducible protein - possible signal peptide† |
| 8566 | | Reg | No Match* |
| 8567 | | Reg | No Match* |
| 8568 | IgSF (YXC) | Reg | integrin (αE)† |
| 8569 | | Reg | No Match* |
| 8570 | | Reg | No Match* |
| 8571 | | Reg | No Match* |
| 8573 | | Reg | alcohol dehydrogenase† |
| 8574 | | Reg | No Match* |
| 8575 | | Reg | No Match* |
| 8589 | NITR (pool of 7) | BFV | 2 IgSF domains; distinct from G7977, G8297a |
| 8590 | | BFV | No Match* |
| 8591 | | BFV | No Match* |
| 8594 | | BFV | No Match* |
| 8606 | NITR (pool of 7) | BFV | 2 IgSF domains; distinct from G7977, G8297A |
| 8608 | | BFV | destabilase† |
| 8609 | | BFV | serine protease (?)† |
| 8610 | | BFV | No Match* |
| 8622 | NITR (pool of 7) | BFV | immunoglobulin superfamily molecule† |

TABLE 2-continued

Beta-lactamase fusion ("Amptrap") PCR-directed sequences

| G# | Target (primer) | Tissue | Comments |
|---|---|---|---|
| 8623 | | BFV | No Match* |
| 8624 | | BFV | Immunoglobulin superfamily molecule† |
| 8625 | | BFV | No Match* |
| 8630 | NITR (pool of 7) | Reg | sorcin (Ca-binding protein)‡ |
| 8631 | | Reg | No Match Unknown human protein* |
| 8632 | | Reg | sorcin (Ca-binding protein)‡ |
| 8633 | | Reg | sorcin (Ca-binding protein)‡ |
| 8634 | | Reg | sorcin (Ca-binding protein)‡ |
| 8635 | | Reg | sorcin (Ca-binding protein)‡ |
| 8636 | | Reg | No Match* |
| 8637 | | Reg | folate receptor† |
| 8658 | NITR (WFK) | BFV | kettin; G8589-like† |
| 8659 | | BFV | immunoglobulin superfamily molecule† |
| 8660 | | BFV | immunoglobulin superfamily molecule† |
| 8661 | | BFV | immunoglobulin superfamily molecule† |
| 8663 | | BFV | immunoglobulin superfamily molecule† |
| 8664 | | BFV | immunoglobulin superfamily molecule† |
| 8665 | | BFV | immunoglobulin superfamily molecule† |
| 8666 | | BFV | RSV receptor - ?† |
| 8667 | | BFV | No Match* |
| 8668 | | BFV | No Match* |
| 8669 | | BFV | immunoglobulin superfamily molecule† |
| 8670 | NITR (WFR1) | BFV | No Match* |
| 8671 | NITR (WFR2) | BFV | No Match* |
| 8673 | | BFV | CD81/CD9† |
| 8694 | NITR? (YWC) | BFV | Lysozyme† |
| 8696 | | BFV | Lysozyme† |
| 8697 | | BFV | Lysozyme† |
| 8698 | | Reg | Repetitive sequence?‡ |
| 8700 | | Reg | No Match hypothetical protein Rv1796 - Mycobacterium tuberculosis -?* |
| 8701 | | Reg | immunoglobulin heavy chain† |
| 8702 | | Reg | No Match* |
| 8704 | | Reg | No Match* |
| 8717 | | Reg | HMG-CoA reductase - ?† |
| 8719 | | Reg | WD40-repeat type I transmembrane protein A72.5† |
| 8720 | | Reg | No Match hypothetical protein Rv1796 - Mycobacterium tuberculosis - ?* |

*No matches to proteins of known function after BLASTX search of Genbank
†Membrane or secreted protein
‡Artifactual sequence (intracellular protein or 3' UTR of cDNA)
OM *Onchorynchus mykiss*, head kidney
DR *Danio rerio*, spleen
BFV *Branchiostoma floridae*, pooled ventral regions
Reg *Raja eglanteria*, spleen
XL *Xenopus laevis*, spleen
PMP *Petromyzon marinus*, protovertebral arch

EXAMPLE 4

Amplification of Candidate Major Histocompatibility Complex (MHC) Genes from *Raja eglanteria*: An Example of PCR Priming Using Only Two Known Amino Acids A PCR primer corresponding to the amino acids cys-X-val (CXV), attached to an SfiI linker (PCR primer, CXV-Sfi: 5'-GACTGGCCGAGGCGGCCCNACNNNRCA-3' (SEQ ID NO. 15)), was used to amplify sequences from *Raja eglanteria* spleen cDNA. Eight Kan$^R$ Amp$^R$ Amptrap clones were sequenced and compared to the Genbank database using the BLASTX algorithm. Five of the eight clones were found to encode an MHC Class II protein (Table 2: 8366–8373).

The CXV amino acid sequence is conserved in the α3 domains of many major histocompatibility complex (MHC) class I proteins, as well as in the α2 domains of MHC class II proteins and $\beta_2$-microglobin ($\beta_2$m). A 3' degenerate primer complementing the CXV motif (described above), in which the second codon position is degenerate (NNN), was used in directed Amptrap analysis of spleen cDNA from the clearnose skate (*Raja eglanteria*, a representative cartilaginous fish (FIG. 7A). The initial PCR reaction produced a broad ethidium bromide-staining band (FIG. 7B). Reaction products were digested with Sfi I and size-selected using a Chromaspin-1000 gel filtration column (CLONTECH) to remove unincorporated primers and very short amplicons before ligation to the Amptrap vector. After transformation and selection on ampicillin plates, eight colonies, containing inserts of at least ~600 bp; were sequenced (FIG. 7C). Five of these colonies were found to encode MHC class II (FIG. 7D). The failure to recover MHC I amplicons was likely due to both size selection bias and the need to change cycling conditions to favor the recovery of longer transcripts (unpublished observations). A similar experiment, in which the gel filtration step was omitted, yielded an amplicon homologous to $\beta_2$m. The predicted coding region of a full-length cDNA encoding the skate homolog of $\beta_2$m contains a 111 amino acid open reading frame that exhibits strong similarity to mammalian $\beta_2$m protein ($p=10^{-11}$–$10^{-12}$). The identities between this gene and other $\beta_2$ ms are shown in FIG. 7E, from which several conclusions can be drawn: 1) highly significant identities exist between skate $\beta_2$m and the other members in this comparison set, 2) several regions of identity between all other $\beta_2$ ms are not shared by skate $\beta_2$m, and 3) several identities are shared by skate $\beta_2$m and some but not all other $\beta_2$ ms.

Therefore, as demonstrated in FIGS. 7A–7E, the methods of the subject invention are particularly useful in cloning divergent members of a gene family using three to five amino acid motifs. At times, the second amino acid can be completely divergent, allowing cloning based on knowledge of only two amino acids, such as described above with respect to the *Raja eglanteria* MHC Class II genes, although the primer should still contain sequences complementary to at least three codons (with the middle sequence being completely degenerate, "NNN", in such a case).

EXAMPLE 5

Amplification of Candidate Genes from Amphioxus

Another example of cloning using the methods of the subject invention is presented in FIGS. 8A–8E. Seven unique primers were designed to complement three to five amino acid motifs surrounding a single conserved tryptophan (W) residue in the N-terminal Ig domains of novel immune-type receptors, which have been interpreted to possibly reflect a conserved feature of primordial immune receptors. These primers were:

```
(1) nitrVYWFR-Sfi (5'-TGGCCGAGGCGGCCCNCGRAACCARTANAC-3';  (SEQ ID NO. 8))

(2) nitrVYWF-Sfi  (5'-GACTGGCCGAGGCGGCCCRAACCARTANAC-3';  (SEQ ID NO. 9))

(3) nitrYWFR-Sfi  (5'-GACTGGCCGAGGCGGCCCNCGRAACCARTA-3';  (SEQ ID NO. 10))

(4) nitrYWFK-swfi (5'-GACTGGCCGAGGCGGCCCYTTRAACCARTA-3';  (SEQ ID NO. 11))

(5) nitrWFR1-Sfi  (5'-GACTGGCCGAGGCGGCCCNCGRAACCA-3';     (SEQ ID NO. 12))

(6) nitrWFR2-Sfi  (5'-GACTGGCCGAGGCGGCCCYCTRAACCA-3'; and (SEQ ID NO. 13))

(7) nitrWFK-Sfi   (5'-GACTGGCCGAGGCGGCCCYTTRAACCA-3'.    (SEQ ID NO. 14))
```

Figure 8A:
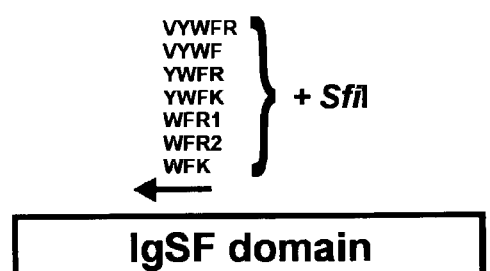
Figure 8B:
Figure 8C:
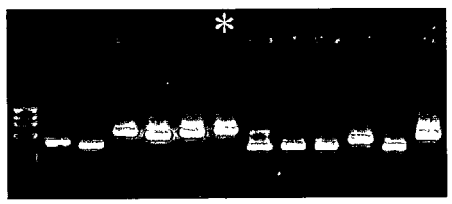

These primers were used in individual reactions to amplify cDNA from amphioxus, as shown in FIG. 8A. The initial 5' RACE PCR produced a 200 bp-2 kilobase (kb) polydisperse distribution of product without any prominent bands, as shown in FIG. 8B). The insert sizes of ampicillin resistant colonies were analyzed directly using PCR (FIG. 8C), and eight colonies containing inserts in the range of ~250–800 bp were selected for sequence analysis. Clone G7977 (FIG. 8D), which was amplified using a degenerate primer corresponding to the amino acid sequence Trp-Phe-Lys (WFK) (primer #7 above), encodes a 57 amino acid open reading frame with similarity to Ig V regions 5' to the primer binding site. Using the G7977 amplicon as a hybridization probe, a full-length cDNA encoding a transmembrane protein bearing an IgSF domain at its N-terminus was isolated, followed by membrane-proximal extracellular domain of unknown function (FIG. 8E). Inspection of the full-length cDNA sequence, recovered separately from the Amptrap PCR, confirmed that the native sequence contains appropriately placed codons for the amino acid sequence WFK.

EXAMPLE 6

Identification of Domains Containing Genes Encoding Chitin Binding Proteins (CBPs)

Figure 9A:
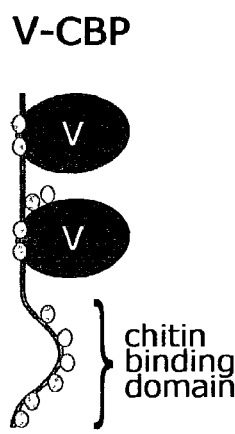
Figure 9C:
Figure 9D:
Figure 9E:
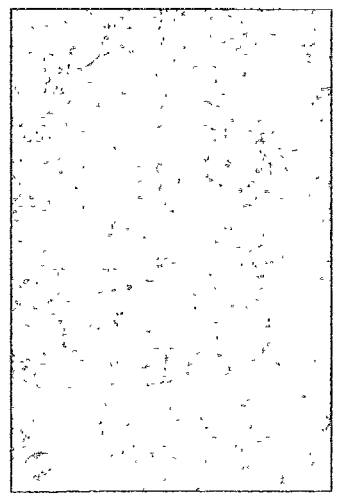

The primers described in Example 5 also permitted the identification of three distinct families of amplicons with ORFs that encode IgSF proteins but do not match known molecules after standard BLASTP searches. These amplicons were labeled individually and used as probes to clone full-length cDNA sequences representing each of the three families. Sequencing of the full-length clones showed that all three families encode putative secreted proteins containing two Ig domains at their N-termini and single putative chitin binding domains at their C-termini, as shown in FIG. 9A. Because of their lengths and the presence of conserved "V" domain amino acids within each domain, the Ig domains of all of these proteins are best classified as "V" type; although similar in structure, the three families, designated V-region containing chitin binding proteins (V-CBPs) share only limited amino acid sequence identity (27–38%). The relationship of these genes to other Ig domain-encoding putative receptors that have been identified in invertebrates is unclear. FIG. 9B shows an amino acid alignment of the V-CBP Ig domains with V domains from mammalian immune receptors. Notably, the sequences exhibit V-type spacing of cysteines and share identity with the additional residues that are most conserved in Ig, TCR, NITRs and other V-type IgSF domains. Subsequent analyses have shown that the V-CBP multigene family is more extensively diversified (data not shown). An expressed recombinant V-CBP (G8297) binds chitin, and this binding is dependent on the presence of the predicted C-terminal chitin-binding domain (FIGS. 9C–9E). Finally, in situ hybridization to mRNA in transverse sections of adult *B. floridae* identified specific expression of G8297 in scattered cells in the intestine; identical hybridization patterns are seen with probes complementing the corresponding regions of the other two V-CBP genes.

Taken together, the above examples of Amptrap cloning demonstrate broad utility based on five successive levels of strong positive selection: 1) enrichment of 5' ends of cDNAs using SMART technology (CLONTECH), 2) requirement for a methionine start codon in the inserted cDNA, 3) requirement for a signal peptide open reading frame downstream of the start codon, 4) requirement for conserved amino acid codons being in-frame with the start codon and open reading frame signal peptide, and 5) requirement for a specified distance between the 5' end of the cDNA and the 3' degenerate primer binding site, which defines a basis for size selection. By requiring a start codon in the cloned sequence, competing artifactual priming is reduced through minimization of introns, intergenic DNA regions and untranslated regions, all of which account for high levels of artifactual amplicons in other PCR-based cloning methods. In each experiment described herein, and numerous other applications (unpublished), relatively few clones are recovered but the frequency of significant targets is very high. In some cases, this integrated series of selection steps can result in the majority of sequenced clones containing inserts with the desired characteristics. In comparing Amptrap cloning to other systems, it is important to recognize that Amptrap is based on selection rather than simple screening; clones encoding irrelevant proteins are deleted from the experiment and do not appear in the pool of colonies for analysis. Amptrap selection for cDNAs allows cloning and selection to occur in bacteria, which are highly amenable to DNA transformation and propagation; clearly such an approach is preferable to yeast selection strategies, which have not received widespread application.

The preceding descriptions of the invention are merely illustrative and should not be considered as limiting the scope of the invention in any way. From the foregoing description, one of ordinary skill in the art can easily ascertain the essential characteristics of the instant invention, and without departing from the spirit and scope thereof, can make various changes and/or modifications of the inventions to adapt it to various usages and conditions. As such, these changes and/or modifications are properly, equitably, and intended to be, within the full range of equivalence of the following claims.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A vector comprising the nucleic acid sequence of SEQ ID NO:1.

2. A method for selecting nucleic acid sequences encoding secreted or membrane-bound proteins which comprises:
   (a) linearizing the vector of claim 1 with one or more restriction enzymes, wherein SEQ ID NO: 1 comprises a reporter gene, a selectable marker gene and a multiple cloning site, wherein the reporter gene encodes β-lactamase lacking a functional signal sequence, and wherein the reporter gene and selectable marker gene are operably linked to a promoter sequence;
   (b) cutting a candidate nucleic acid sequence with the one or more restriction enzymes and ligating the candidate nucleic acid sequence to the linearized vector, thereby forming a ligation product, wherein the candidate nucleic acid sequence encodes a potential secreted or membrane-bound protein;
   (c) transforming bacterial cells with the ligation product; and
   (d) selecting for colonies based on export of β-lactamase to the periplasmic space of the bacterial cells.

3. A method for selecting nucleic acid sequences encoding secreted or membrane-bound proteins which comprises:
   (a) providing the vector of claim 1, wherein the vector is linearized, wherein SEQ ID NO: 1 comprises a reporter gene, a selectable marker gene and a multiple cloning site, wherein the reporter gene encodes β-lactamase lacking a functional signal sequence, and wherein the reporter gene and selectable marker gene are operably linked to a promoter sequence;
   (b) ligating a candidate nucleic acid sequence to the linearized vector, thereby forming a ligation product, wherein the candidate nucleic acid sequence encodes a potential secreted or membrane-bound protein;
   (c) transforming bacterial cells with the ligation product; and
   (d) selecting for colonies based on export of β-lactamase to the periplasmic space of the bacterial cells.

4. A vector comprising the nucleic acid sequence of SEQ ID NO. 2.

5. A method for selecting nucleic acid sequences encoding secreted or membrane-bound proteins which comprises:
   (a) linearizing the vector of claim 4 with one or more restriction enzymes, wherein SEQ ID NO: 2 comprises a reporter gene, a selectable marker gene and a multiple cloning site, wherein the reporter gene encodes β-lactamase lacking a functional signal sequence, and wherein the reporter gene and selectable marker gene are operably linked to a promoter sequence;
   (b) cutting a candidate nucleic acid sequence with the one or more restriction enzymes and ligating the candidate nucleic acid sequence to the linearized vector, thereby forming a ligation product, wherein the candidate nucleic acid sequence encodes a potential secreted or membrane-bound protein;
   (c) transforming bacterial cells with the ligation product; and
   (d) selecting for colonies based on export of β-lactamase to the periplasmic space of the bacterial cells.

6. A method for selecting nucleic acid sequences encoding secreted or membrane-bound proteins which comprises:
   (a) providing the vector of claim 4, wherein the vector is linearized, wherein SEQ ID NO: 1 comprises a reporter gene, a selectable marker gene and a multiple cloning site, wherein the reporter gene encodes β-lactamase lacking a functional signal sequence, and wherein the reporter gene and selectable marker gene are operably linked to a promoter sequence;
   (b) ligating a candidate nucleic acid sequence to the linearized vector, thereby forming a ligation product, wherein the candidate nucleic acid sequence encodes a potential secreted or membrane-bound protein;
   (c) transforming bacterial cells with the ligation product; and
   (d) selecting for colonies based on export of β-lactamase to the periplasmic space of the bacterial cells.

* * * * *

UNITED STATES PATENT AND TRADEMARK OFFICE
CERTIFICATE OF CORRECTION

| | | |
|---|---|---|
| PATENT NO. | : 7,112,434 B2 | Page 1 of 1 |
| APPLICATION NO. | : 10/138998 | |
| DATED | : September 26, 2006 | |
| INVENTOR(S) | : John P. Cannon, Robert N. Haire and Gary W. Litman | |

It is certified that error appears in the above-identified patent and that said Letters Patent is hereby corrected as shown below:

Column 5,
Line 4, "methods of the subject invention.

DETAILED DISCLOSURE OF THE INVENTION"

should read

--methods of the subject invention.
    SEQ ID NOs. 16-19 are amino acid motifs surrounding a single conserved tryptophan (W) residue in the N-terminal Ig domains of immune-type receptors, as shown in Figure 8A.

DETAILED DISCLOSURE OF THE INVENTION--.

Signed and Sealed this

Twenty-second Day of May, 2007

JON W. DUDAS
*Director of the United States Patent and Trademark Office*

UNITED STATES PATENT AND TRADEMARK OFFICE
CERTIFICATE OF CORRECTION

PATENT NO. : 7,112,434 B2 Page 1 of 1
APPLICATION NO. : 10/138998
DATED : September 26, 2006
INVENTOR(S) : John P. Cannon, Robert N. Haire and Gary W. Litman It is certified that error appears in the above-identified patent and that said Letters Patent is hereby corrected as shown below:

Column 1
Lines 21 - 22, "government may have certain" should read -- government has certain --.

Signed and Sealed this

Twenty-first Day of April, 2009

JOHN DOLL
*Acting Director of the United States Patent and Trademark Office*

SEQUENCE LISTING

```
<160> NUMBER OF SEQ ID NOS: 19

<210> SEQ ID NO 1
<211> LENGTH: 4778
<212> TYPE: DNA
<213> ORGANISM: Artificial Sequence
<220> FEATURE:
<223> OTHER INFORMATION: Cloning Vector G7311
<220> FEATURE:
<221> NAME/KEY: misc_feature
<222> LOCATION: (126)..(1187)
<223> OTHER INFORMATION: neomycin resistance gene
<220> FEATURE:
<221> NAME/KEY: promoter
<222> LOCATION: (2637)..(2758)
<223> OTHER INFORMATION: lac promoter
<220> FEATURE:
<221> NAME/KEY: misc_feature
<222> LOCATION: (2815)..(2889)
<223> OTHER INFORMATION: multiple cloning site
<220> FEATURE:
<221> NAME/KEY: misc_feature
<222> LOCATION: (2897)..(3688)
<223> OTHER INFORMATION: signal-less beta lactamase gene

<400> SEQUENCE: 1 gcactttcg gggaaatgtg cgcggaaccc ctatttgttt attttctaa atacattcaa      60 atatgtatcc gctcatgaga caataaccct gataaatgct tcaataatat tgaaaaagga    120
agagtcctga ggaagcgaac cggaattgcc agctggggcg ccctctggta aggttgggaa    180
gccctgcaaa gtaaactgga tggctttctc gccgccaagg atctgatggc gcagggatc     240 aagctctgat caagagacag gatgaggatc gtttcgcatg attgaacaag atggattgca    300
cgcaggttct ccggccgctt gggtggagag gctattcggc tatgactggg cacaacagac    360
aatcggctgc tctgatgccg ccgtgttccg gctgtcagcg caggggcgcc cggttctttt    420
tgtcaagacc gacctgtccg gtgccctgaa tgaactgcaa gacgaggcag cgcggctatc    480
gtggctggcc acgacgggcg ttccttgcgc agctgtgctc gacgttgtca ctgaagcggg    540
aagggactgg ctgctattgg gcgaagtgcc ggggcaggat ctcctgtcat ctcaccttgc    600
tcctgccgag aaagtatcca tcatggctga tgcaatgcgg cggctgcata cgcttgatcc    660
ggctacctgc ccattcgacc accaagcgaa acatcgcatc gagcgagcac gtactcggat    720
ggaagccggt cttgtcgatc aggatgatct ggacgaagag catcaggggc tcgcgccagc    780
cgaactgttc gccaggctca aggcgagcat gcccgacggc gaggatctcg tcgtgaccca    840
tggcgatgcc tgcttgccga atatcatggt ggaaaatggc cgcttttctg gattcatcga    900
ctgtggccgg ctgggtgtgg cggaccgcta tcaggacata gcgttggcta cccgtgatat    960
tgctgaagag cttggcggcg aatgggctga ccgcttcctc gtgctttacg gtatcgccgc   1020
tcccgattcg cagcgcatcg ccttctatcg ccttcttgac gagttcttct gaattattaa   1080
cgcttacaat ttcctgatgc ggtattttct ccttacgcat ctgtgcggta tttcacaccg   1140 catacaggt gcacttttcg gggaaatgtg cgcggaaccc cctcaggtta ctcatatata   1200
ctttagattg atttaaaact tcattttaa tttaaaagga tctaggtgaa gatcctttt    1260
```

```
gataatctca tgaccaaaat cccttaacgt gagttttcgt tccactgagc gtcagacccc    1320
gtagaaaaga tcaaaggatc ttcttgagat cctttttttc tgcgcgtaat ctgctgcttg    1380
caaacaaaaa aaccaccgct accagcggtg gtttgtttgc cggatcaaga gctaccaact    1440 cttttttccga aggtaactgg cttcagcaga gcgcagatac caaatactgt ccttctagtg    1500
tagccgtagt taggccacca cttcaagaac tctgtagcac cgcctacata cctcgctctg    1560
ctaatcctgt taccagtggc tgctgccagt ggcgataagt cgtgtcttac cgggttggac    1620
tcaagacgat agttaccgga taaggcgcag cggtcgggct gaacggggggg ttcgtgcaca    1680 cagcccagct tggagcgaac gacctacacc gaactgagat acctacagcg tgagctatga    1740
gaaagcgcca cgcttcccga agggagaaag gcggacaggt atccggtaag cggcagggtc    1800
ggaacaggag agcgcacgag ggagcttcca gggggaaacg cctggtatct ttatagtcct    1860
gtcgggtttc gccacctctg acttgagcgt cgatttttgt gatgctcgtc agggggggcgg    1920 agcctatgga aaaacgccag caacgcggcc ttttacggtt cctggccttt tgctggcct     1980 tttgctcaca tgttctttcc tgcgttatcc cctgattctg tggataaccg tattaccgcc    2040
atgcattagt tattaatagt aatcaattac ggggtcatta gttcatagcc catatatgga    2100
gttccgcgtt acataactta cggtaaatgg cccgcctggc tgaccgccca cgacccccg     2160 cccattgacg tcaataatga cgtatgttcc catagtaacg ccaataggga ctttccattg    2220
acgtcaatgg gtggagtatt tacggtaaac tgcccacttg gcagtacatc aagtgtatca    2280
tatgccaagt acgccccta ttgacgtcaa tgacggtaaa tggcccgcct ggcattatgc     2340
ccagtacatg accttatggg acttttcctac ttggcagtac atctacgtat tagtcatcgc   2400
tattaccatg gtgatgcggt tttggcagta catcaatggg cgtggatagc ggtttgactc    2460
acggggattt ccaagtctcc accccattga cgtcaatggg agtttgtttt ggcaccaaaa    2520
tcaacgggac tttccaaaat gtcgtaacaa ctccgcccca ttgacgcaaa tgggcggtag    2580
gcgtgtacgg tgggaggtct atataagcag agctggttta gtgaaccgtc agatccgcta    2640
gccgcaatta ctgtgagtta gctcactcat taggcacccc aggctttaca ctttatactt    2700
ccggctcgta tattgtgtgg aattgtgagc ggataacaat ttcacacagg aaacagctat    2760
gaccttgatt acgccaagct cgaaattaac cctcactaaa gggaacaaaa gctgagctc     2820 caccgcggat tgatagtaag gccattatgg ccgaattcgg ccgcctcggc cggatccccc    2880
gggctgcagg aattcgcacc cagaaacgct ggtgaaagta aaagatgctg aagatcagtt    2940
gggtgcacga gtgggttaca tcgaactgga tctcaacagc ggtaagatcc ttgagagttt    3000
tcgccccgaa gaacgttttc caatgatgag cacttttaaa gttctgctat gtggcgcggt    3060
attatcccgt attgacgccg ggcaagagca actcggtcgc cgcatacact attctcagaa    3120
tgacttggtt gagtactcac cagtcacaga aaagcatctt acggatggca tgacagtaag    3180
agaattatgc agtgctgcca taaccatgag tgataacact gcggccaact tacttctgac    3240
aacgatcgga ggaccgaagg agctaaccgc ttttttgcac aacatggggg atcatgtaac    3300
tcgccttgat cgttgggaac cggagctgaa tgaagccata ccaaacgacg agcgtgacac    3360
cacgatgcct gtagcaatgg caacaacgtt gcgcaaacta ttaactggcg aactacttac    3420
tctagcttcc cggcaacaat taatagactg gatggaggcg gataaagttg caggaccact    3480
tctgcgctcg gcccttccgg ctggctggtt tattgctgat aaatctggag ccggtgagcg    3540
tgggtctcgc ggtatcattg cagcactggg gccagatggt aagccctccc gtatcgtagt    3600
tatctacacg acggggagtc aggcaactat ggatgaacga aatagacaga tcgctgagat    3660
```

```
aggtgcctca ctgattaagc attggtaaga attcgatatc aagcttataa cttcgtatag    3720
cagcatacat tatacgaagt tatctcgagg ggggccgg taccaggtaa gtgtacccaa      3780
```
*(note: line 3780 as printed)*
```
ttcgccctat agtgagtcgt attacaattc actggccgtc gttttacaac gtcgtgactg    3840
ggaaaaccct ggcgttaccc aacttaatcg ccttgcagca catcccccctt cgccagctg     3900 gcgtaatagc gaagaggccc gcaccgatcg cccttcccaa cagttgcgca gcctgaatgg    3960
cgaatggaga tccaattttt aagtgtataa tgtgttaaac tactgattct aattgtttgt    4020 gtatttaga ttcacagtcc caaggctcat ttcaggcccc tcagtcctca cagtctgttc      4080
atgatcataa tcagccatac cacatttgta gaggttttac ttgctttaaa aaacctccca    4140
cacctccccc tgaacctgaa acataaaatg aatgcaattg ttgttgttaa cttgtttatt     4200
gcagcttata atggttacaa ataaagcaat agcatcacaa atttcacaaa taaagcattt    4260
ttttcactgc attctagttg tggtttgtcc aaactcatca atgtatctta acgcgtaaat    4320
tgtaagcgtt aatattttgt taaaattcgc gttaaatttt tgttaaatca gctcattttt   4380
taaccaatag gccgaaatcg gcaaaatccc ttataaatca aaagaataga ccgagatagg    4440
gttgagtgtt gttccagttt ggaacaagag tccactatta agaacgtgg actccaacgt     4500 caaagggcga aaaccgtct atcagggcga tggcccacta cgtgaaccat caccctaatc     4560
aagttttttg gggtcgaggt gccgtaaagc actaaatcgg aaccctaaag ggagccccg     4620 atttagagct tgacgggaa agccggcgaa cgtggcgaga aggaaggga agaaagcgaa      4680 aggagcgggc gctagggcgc tggcaagtgt agcggtcacg ctgcgcgtaa ccaccacacc    4740
cgccgcgctt aatgcgccgc tacagggcgc gtcaggtg                            4778
```

<210> SEQ ID NO 2
<211> LENGTH: 4782
<212> TYPE: DNA
<213> ORGANISM: Artificial Sequence
<220> FEATURE:
<223> OTHER INFORMATION: Cloning Vector G7637
<220> FEATURE:
<221> NAME/KEY: misc_feature
<222> LOCATION: (126)..(1187)
<223> OTHER INFORMATION: neomycin resistance gene
<220> FEATURE:
<221> NAME/KEY: promoter
<222> LOCATION: (2637)..(2758)
<223> OTHER INFORMATION: lac promoter
<220> FEATURE:
<221> NAME/KEY: misc_feature
<222> LOCATION: (2815)..(2879)
<223> OTHER INFORMATION: multiple cloning site
<220> FEATURE:
<221> NAME/KEY: misc_feature
<222> LOCATION: (2880)..(2892)
<223> OTHER INFORMATION: SLIP sequence
<220> FEATURE:
<221> NAME/KEY: misc_feature
<222> LOCATION: (2901)..(3692)
<223> OTHER INFORMATION: signal-less beta lactamase gene

<400> SEQUENCE: 2

```
gcacttttcg gggaaatgtg cgcggaaccc ctatttgttt attttttctaa atacattcaa    60 atatgtatcc gctcatgaga caataaccct gataaatgct tcaataatat tgaaaaagga   120
agagtcctga ggaagcgaac cggaattgcc agctggggcg ccctctggta aggttgggaa   180
gccctgcaaa gtaaactgga tgctttctc gccgccaagg atctgatggc gcaggggatc    240
aagctctgat caagagacag gatgaggatc gtttcgcatg attgaacaag atggattgca   300
```

-continued

```
cgcaggttct ccggccgctt gggtggagag gctattcggc tatgactggg cacaacagac      360
aatcggctgc tctgatgccg ccgtgttccg gctgtcagcg caggggcgcc cggttctttt      420
tgtcaagacc gacctgtccg gtgccctgaa tgaactgcaa gacgaggcag cgcggctatc      480
gtggctggcc acgacgggcg ttccttgcgc agctgtgctc gacgttgtca ctgaagcggg      540
aagggactgg ctgctattgg gcgaagtgcc ggggcaggat ctcctgtcat ctcaccttgc      600
tcctgccgag aaagtatcca tcatggctga tgcaatgcgg cggctgcata cgcttgatcc      660
ggctacctgc ccattcgacc accaagcgaa acatcgcatc gagcgagcac gtactcggat      720
ggaagccggt cttgtcgatc aggatgatct ggacgaagag catcagggc tcgcgccagc       780 cgaactgttc gccaggctca aggcgagcat gcccgacggc gaggatctcg tcgtgaccca      840
tggcgatgcc tgcttgccga atatcatggt ggaaaatggc cgcttttctg gattcatcga      900
ctgtggccgg ctgggtgtgg cggaccgcta tcaggacata gcgttggcta cccgtgatat      960
tgctgaagag cttggcggcg aatgggctga ccgcttcctc gtgctttacg gtatcgccgc     1020
tcccgattcg cagcgcatcg ccttctatcg ccttcttgac gagttcttct gaattattaa     1080
cgcttacaat ttcctgatgc ggtattttct ccttacgcat ctgtgcggta tttcacaccg     1140
catacaggtg gcacttttcg gggaaatgtg cgcggaaccc cctcaggtta ctcatatata     1200
ctttagattg atttaaaact tcatttttaa tttaaaagga tctaggtgaa gatcctttt      1260 gataatctca tgaccaaaat cccttaacgt gagttttcgt tccactgagc gtcagacccc     1320
gtagaaaaga tcaaaggatc ttcttgagat ccttttttc tgcgcgtaat ctgctgcttg     1380
caaacaaaaa aaccaccgct accagcggtg gtttgtttgc cggatcaaga gctaccaact     1440
ctttttccga aggtaactgg cttcagcaga gcgcagatac caaatactgt ccttctagtg     1500
tagccgtagt taggccacca cttcaagaac tctgtagcac cgcctacata cctcgctctg     1560
ctaatcctgt taccagtggc tgctgccagt ggcgataagt cgtgtcttac cgggttggac     1620
tcaagacgat agttaccgga taaggcgcag cggtcgggct gaacggggg ttcgtgcaca      1680 cagcccagct tggagcgaac gacctacacc gaactgagat acctacagcg tgagctatga     1740
gaaagcgcca cgcttcccga agggagaaag gcggacaggt atccgtaag cggcagggtc      1800 ggaacaggag agcgcacgag ggagcttcca gggggaaacg cctggtatct ttatagtcct     1860
gtcgggtttc gccacctctg acttgagcgt cgatttttgt gatgctcgtc agggggggcgg    1920 agcctatgga aaaacgccag caacgcggcc ttttacggt tcctggcctt ttgctggcct      1980
tttgctcaca tgttctttcc tgcgttatcc cctgattctg tggataaccg tattaccgcc     2040
atgcattagt tattaatagt aatcaattac ggggtcatta gttcatagcc catatatgga     2100
gttccgcgtt acataactta cggtaaatgg cccgcctggc tgaccgccca acgacccccg     2160
cccattgacg tcaataatga cgtatgttcc catagtaacg ccaatagga ctttccattg      2220 acgtcaatgg gtggagtatt tacggtaaac tgcccacttg gcagtacatc aagtgtatca     2280
tatgccaagt acgcccccta ttgacgtcaa tgacggtaaa tggcccgcct ggcattatgc     2340
ccagtacatg accttatggg actttcctac ttggcagtac atctacgtat tagtcatcgc     2400
tattaccatg gtgatgcggt tttggcagta catcaatggg cgtggatagc ggtttgactc     2460
acggggattt ccaagtctcc accccattga cgtcaatggg agtttgtttt ggcaccaaaa     2520
tcaacgggac tttccaaaat gtcgtaacaa ctccgcccca ttgacgcaaa tgggcggtag     2580
gcgtgtacgg tgggaggtct atataagcag agctggttta gtgaaccgtc agatccgcta     2640
gccgcaatta ctgtgagtta gctcactcat taggcacccc aggctttaca ctttatactt     2700
```

```
ccggctcgta tattgtgtgg aattgtgagc ggataacaat tcacacagg aaacagctat    2760
gaccttgatt acgccaagct cgaaattaac cctcactaaa gggaacaaaa gctggagctc    2820
caccgcggat tgatagtaag gccattatgg ccgaattcgg ccgcctcggc cggatccaat    2880
tttttttttt ttggaattcg cacccagaaa cgctggtgaa agtaaaagat gctgaagatc    2940
agttgggtgc acgagtgggt tacatcgaac tggatctcaa cagcgtaag atccttgaga     3000
gttttcgccc cgaagaacgt tttccaatga tgagcacttt taaagttctg ctatgtggcg    3060
cggtattatc ccgtattgac gccgggcaag agcaactcgg tcgccgcata cactattctc    3120
agaatgactt ggttgagtac tcaccagtca cagaaaagca tcttacggat ggcatgacag    3180
taagagaatt atgcagtgct gccataacca tgagtgataa cactgcggcc aacttacttc    3240
tgacaacgat cggaggaccg aaggagctaa ccgcttttt gcacaacatg ggggatcatg     3300
taactcgcct tgatcgttgg aaccggagc tgaatgaagc cataccaaac gacgagcgtg     3360
acaccacgat gcctgtagca atggcaacaa cgttgcgcaa actattaact ggcgaactac    3420
ttactctagc ttcccggcaa caattaatag actggatgga ggcggataaa gttgcaggac    3480
cacttctgcg ctcggcccctt ccggctggct ggtttattgc tgataaatct ggagccggtg   3540
agcgtgggtc tcgcggtatc attgcagcac tggggccaga tggtaagccc tcccgtatcg    3600
tagttatcta cacgacgggg agtcaggcaa ctatggatga acgaaataga cagatcgctg    3660
agataggtgc ctcactgatt aagcattggt aagaattcga tatcaagctt ataacttcgt    3720
atagcagcat acattatacg aagttatctc gagggggggc ccggtaccag gtaagtgtac    3780
ccaattcgcc ctatagtgag tcgtattaca attcactggc cgtcgtttta caacgtcgtg    3840
actgggaaaa cctggcgtt acccaactta atcgccttgc agcacatccc ctttcgcca     3900
gctggcgtaa tagcgaagag gcccgcaccg atcgcccttc ccaacagttg cgcagcctga    3960
atggcgaatg gagatccaat tttaagtgt ataatgtgtt aaactactga ttctaattgt     4020
ttgtgtattt tagattcaca gtcccaaggc tcatttcagg cccctcagtc ctcacagtct    4080
gttcatgatc ataatcagcc ataccacatt tgtagaggtt ttacttgctt taaaaaacct    4140
cccacacctc ccctgaacc tgaaacataa aatgaatgca attgttgttg ttaacttgtt    4200
tattgcagct tataatggtt acaaataaag caatagcatc acaaatttca caataaagc    4260
attttttttca ctgcattcta gttgtggttt gtccaaactc atcaatgtat cttaacgcgt    4320
aaattgtaag cgttaatatt ttgttaaaat tcgcgttaaa ttttttgttaa atcagctcat    4380
tttttaacca ataggccgaa atcggcaaaa tcccttataa atcaaaagaa tagaccgaga    4440
tagggttgag tgttgttcca gtttggaaca agagtccact attaaagaac gtggactcca    4500
acgtcaaagg gcgaaaaacc gtctatcagg gcgatggccc actacgtgaa ccatcaccct    4560
aatcaagttt ttggggtcg aggtgccgta aagcactaaa tcggaaccct aaagggagcc     4620
cccgatttag agcttgacgg ggaaagccgg cgaacgtggc gagaaaggaa gggaagaaag    4680
cgaaaggagc gggcgctagg gcgctggcaa gtgtagcggt cacgctgcgc gtaaccacca    4740
cacccgccgc gcttaatgcg ccgctacagg gcgcgtcagg tg                       4782
```

<210> SEQ ID NO 3  
<211> LENGTH: 333  
<212> TYPE: PRT  
<213> ORGANISM: Branchiostoma floridae  
<220> FEATURE:  
<221> NAME/KEY: MISC_FEATURE  
<222> LOCATION: (1)..(333)

<223> OTHER INFORMATION: V-CBP3

<400> SEQUENCE: 3

Met Gln Met Phe Leu Leu Val Ser Val Cys Leu Gly Met Ala Tyr Gly
1               5                   10                  15

Gln Ser Ile Met Thr Val Arg Thr Thr His Thr Glu Val Glu Val His
            20                  25                  30

Ala Gly Gly Thr Val Glu Leu Pro Cys Ala Tyr Gln Leu Ala Asn Asp
        35                  40                  45

Thr Gln Pro Pro Val Ile Ser Trp Leu Lys Gly Ala Arg Arg Thr Glu
    50                  55                  60

Ala Pro Arg Ser Ser Arg Glu Thr Thr Gly Arg Glu Arg Gly Trp
65                  70                  75                  80

Gly Ser Trp Arg Ala Thr Asp Lys Glu Ser Phe Gly Asp Phe Leu Gly
                85                  90                  95

Arg Ala Ser Val Ala Asn Leu Ala Ala Pro Thr Leu Arg Leu Thr His
            100                 105                 110

Val His Pro Gln Asp Gly Gly Arg Tyr Trp Cys Gln Val Ala Gln Trp
        115                 120                 125

Ser Ile Arg Thr Glu Phe Gly Leu Asp Ala Lys Ser Val Val Leu Lys
    130                 135                 140

Val Thr Gly His Thr Pro Ser Asn Asn Val His Val Ser Thr Ala Glu
145                 150                 155                 160

Val Val Gln Val Asp Glu Gly Asn Asp Ile Thr Met Thr Cys Pro Cys
                165                 170                 175

Thr Asp Cys Ala Asn Ala Asn Val Thr Trp Tyr Thr Gly Pro Thr Phe
            180                 185                 190

Phe Glu Asn Tyr Glu Thr Gly Thr Tyr Gln Pro Leu Pro Thr Arg Thr
        195                 200                 205

Ser Ser Ala Ser Pro Gly Ser Arg Leu Arg Ser Arg Ala Gly Arg Ala
    210                 215                 220

Ser Ala Ala Arg Gly Thr Trp Ser Ser Gly Pro Pro Arg Ser Thr Asp
225                 230                 235                 240

Ala Gly Arg Val Trp Cys Glu Leu Ala Thr Gly Gln Gly Glu Leu Asp
                245                 250                 255

Ala Asp Arg Ser Ser Thr Ile Leu Lys Val Gln Leu Glu Pro Phe Thr
            260                 265                 270

Cys Asp Gly Lys Pro Thr Gly Leu Tyr Ala Asp Pro Thr Ala Cys Asp
        275                 280                 285

Tyr Tyr Tyr Gln Cys Ile Pro Gly Tyr Pro Pro Leu His Arg Pro Cys
    290                 295                 300

Gly Tyr Ala Gly Met Val Phe Asn Glu Glu Met Gln Tyr Cys Asp Trp
305                 310                 315                 320

Asp Ile Asn Val Pro Pro Pro Cys Gly Ser Lys Pro Val
                325                 330

<210> SEQ ID NO 4
<211> LENGTH: 333
<212> TYPE: PRT
<213> ORGANISM: Branchiostoma floridae
<220> FEATURE:
<221> NAME/KEY: MISC_FEATURE
<222> LOCATION: (1)..(333)
<223> OTHER INFORMATION: V-CBP1

<400> SEQUENCE: 4

```
Met Lys Phe Val Leu Gly Leu Val Leu Leu Ala Val Gly Ala His Ala
1               5                   10                  15

Met Thr Ile Val Thr Val Ser Thr Pro Glu Pro Lys Val Glu Ala Ser
            20                  25                  30

Val Gly Gly Ser Ala Glu Leu Lys Cys Glu Phe Asp Ile Gln Pro Asn
        35                  40                  45

Ser Thr Gln Pro Pro Thr Ile Ala Trp Phe Lys Gly Asn Asp Asp Phe
50                      55                  60

Arg Gly Val Glu Arg Ile Tyr Thr Gly His Lys Val Trp Gly Asn Glu
65                  70                  75                  80

Thr Glu Arg Arg Glu Asp Ser Phe Gly Asp Tyr Ile Gly Arg Val Glu
                85                  90                  95

Val Ala Asp Leu Asp Lys Pro Ala Ile Lys Ile Ser Gly Ile Lys Ser
            100                 105                 110

Thr Asp Phe Ala Arg Tyr Trp Cys Thr Val Ala Glu Trp Gly Val Arg
        115                 120                 125

Thr Glu Leu Gly Val Asp Ala Lys Ser Val Leu Leu Thr Glu Thr Gly
130                     135                 140

His Ser Glu Ala Ser Ile Asp Ile Ser Val Ser Gly Glu Lys Asp Val
145                 150                 155                 160

Glu Glu Gly Gly Asp Val Glu Met Thr Cys Arg Cys His Gly Cys Thr
                165                 170                 175

Ser Ala Ala Ile Phe Asp Trp Phe Lys Gly Ala Phe Ala Gly Ser Glu
            180                 185                 190

Trp Val Thr Thr Gly Asn Tyr Thr His Ile Ala Ala Lys Val Asp Val
        195                 200                 205

Gly Val Leu Gly Phe Pro Asn Pro Ile Glu Ile Asp Asp Gly Phe Gly
210                     215                 220

Gln Phe Ser Val Thr Pro Ser Asn Ser Leu Arg Leu Thr Gly Ala Gln
225                 230                 235                 240

Val Ala Asp Ala Gly Arg Tyr Trp Cys Lys Val Thr Ser Gly Gly Ser
                245                 250                 255

Val Asp Ile Lys Ala Thr Val Leu Lys Val Lys Val Pro Glu Phe Thr
            260                 265                 270

Cys Ala Gly Lys Ala Asp Gly Tyr Tyr Pro Asp Pro Glu Asp Cys Ala
        275                 280                 285

Met Tyr Tyr Gln Cys Leu Tyr Gly Phe Pro Gln Pro Phe His Arg Pro
290                 295                 300

Cys Gly Tyr Ala Gly Met Val Phe Asn Pro Glu His Leu Tyr Cys Asp
305                 310                 315                 320

Trp Ala Phe Asn Val Gly Pro Pro Cys Gly Ser Lys Ala
            325                 330

<210> SEQ ID NO 5
<211> LENGTH: 350
<212> TYPE: PRT
<213> ORGANISM: Branchiostoma floridae
<220> FEATURE:
<221> NAME/KEY: MISC_FEATURE
<222> LOCATION: (1)..(350)
<223> OTHER INFORMATION: V-CBP2

<400> SEQUENCE: 5

Met Leu Gly Leu Leu Val Ala Ile Ser Ala Val Ala Cys Phe Glu Ser
1               5                   10                  15

Ser Tyr Ala Asp Ala Val Ser Ile Thr Asn Val Thr Ala Pro Tyr Arg
```

```
            20                  25                  30
Gly Ser Trp Val Met Ile Trp Asn Thr Trp Asp Pro Thr Trp Val
        35                  40                  45
Asn Arg Val Glu Ile Gly Cys Glu Tyr Thr Ile Ser Pro Ala Pro Ala
 50                  55                  60
Thr Pro Pro Thr Ile Thr Trp Leu Lys Gly Ser Phe Thr Asp Arg Gln
 65                  70                  75                  80
Val Ile Tyr Lys Leu Thr Ser Ser Gly Glu Val Tyr Val His Pro Glu
                 85                  90                  95
Tyr Ala Gly Arg Val Ser Val Pro Ser Arg Thr His Pro Thr Leu Val
            100                 105                 110
Leu Thr Asp Ser Lys Phe Asp Asp Trp Gly Arg Tyr Trp Cys Arg Val
            115                 120                 125
Thr Asn Glu Glu Gln Ser Asp Asp Phe Gly Thr Asp Glu Glu Ser Arg
130                 135                 140
Leu Phe Trp Phe Lys Ser Gly Tyr Asp Pro Ala Arg Gly Ser His Tyr
145                 150                 155                 160
Ser Phe Val Gln Val Asp Lys Thr Pro Val Arg Val Lys Thr Gly Gly
                165                 170                 175
Thr Ala Lys Leu His Cys Glu Gly Trp Gly Lys Ser Ala Ser Ile
            180                 185                 190
Val Trp Phe Lys Gly Pro Ser Cys Thr Gln Asp Gly Asn Cys Asn Val
            195                 200                 205
Tyr Glu Met Val Ile Asn Lys Thr Ala Val Glu His Phe Ser Pro Asp
            210                 215                 220
Pro Gly Thr Val Asn Val Ser Pro Asn Tyr Ala Gly Arg Ala Ser Leu
225                 230                 235                 240
Gly Ala Asn Asn Met Gly Tyr Thr Leu Asp Leu Thr Ile Thr Asp Ile
                245                 250                 255
Arg Pro Ala Asp Val Gly Arg Tyr Trp Cys Thr Asn Asp Trp Pro Leu
            260                 265                 270
Tyr Phe Arg Asn Glu Val Gln Ser Arg Asp Ser Gln Ser Val Val Val
            275                 280                 285
Leu Leu Asp Asp Glu Ala Pro Ser Cys Asp Gly Lys Ala Asp Gly Met
290                 295                 300
Tyr Gln Asp Pro Gly Asp Cys Ser Arg Tyr Tyr Thr Cys Ser Gly Gly
305                 310                 315                 320
Trp Leu Tyr Gly Pro Val Pro Cys Ile Ser Gly Leu Phe Phe Asn Glu
                325                 330                 335
Ala Leu Gln Val Cys Asp Trp Pro Asn Asn Val Ala Cys Val
            340                 345                 350
```

<210> SEQ ID NO 6
<211> LENGTH: 13
<212> TYPE: DNA
<213> ORGANISM: Artificial Sequence
<220> FEATURE:
<223> OTHER INFORMATION: Sfi I endonuclease site
<220> FEATURE:
<221> NAME/KEY: misc_feature
<222> LOCATION: (5)..(9)
<223> OTHER INFORMATION: n = a, c, g, or t.

<400> SEQUENCE: 6
ggccnnnnng gcc                                                       13

```
<210> SEQ ID NO 7
<211> LENGTH: 23
<212> TYPE: DNA
<213> ORGANISM: Artificial Sequence
<220> FEATURE:
<223> OTHER INFORMATION: synthetic oligonucleotide SMART-DNA

<400> SEQUENCE: 7
aagcagtggt atcaacgcag agt                                             23

<210> SEQ ID NO 8
<211> LENGTH: 30
<212> TYPE: DNA
<213> ORGANISM: Artificial Sequence
<220> FEATURE:
<223> OTHER INFORMATION: synthetic oligonucleotide nitrVYWFR-Sfi
<220> FEATURE:
<221> NAME/KEY: misc_feature
<222> LOCATION: (16)..(16)
<223> OTHER INFORMATION: n = a, c, g, or t.
<220> FEATURE:
<221> NAME/KEY: misc_feature
<222> LOCATION: (28)..(28)
<223> OTHER INFORMATION: n = a, c, g, or t.

<400> SEQUENCE: 8
tggccgaggc ggcccncgra accartanac                                      30

<210> SEQ ID NO 9
<211> LENGTH: 30
<212> TYPE: DNA
<213> ORGANISM: Artificial Sequence
<220> FEATURE:
<223> OTHER INFORMATION: synthetic oligonucleotide nitrVYWF-Sfi
<220> FEATURE:
<221> NAME/KEY: misc_feature
<222> LOCATION: (28)..(28)
<223> OTHER INFORMATION: n = a, c, g, or t.

<400> SEQUENCE: 9
gactggccga ggcggcccra accartanac                                      30

<210> SEQ ID NO 10
<211> LENGTH: 30
<212> TYPE: DNA
<213> ORGANISM: Artificial Sequence
<220> FEATURE:
<223> OTHER INFORMATION: synthetic oligonucleotide nitrYWFR-Sfi
<220> FEATURE:
<221> NAME/KEY: misc_feature
<222> LOCATION: (19)..(19)
<223> OTHER INFORMATION: n = a, c, g, or t.

<400> SEQUENCE: 10
gactggccga ggcggcccnc graaccarta                                      30

<210> SEQ ID NO 11
<211> LENGTH: 30
<212> TYPE: DNA
<213> ORGANISM: Artificial Sequence
<220> FEATURE:
<223> OTHER INFORMATION: synthetic oligonucleotide nitrYWFK-Sfi

<400> SEQUENCE: 11
gactggccga ggcggcccyt traaccarta                                      30

<210> SEQ ID NO 12
<211> LENGTH: 27
<212> TYPE: DNA
```

<210> SEQ ID NO 12
<211> LENGTH: 27
<212> TYPE: DNA
<213> ORGANISM: Artificial Sequence
<220> FEATURE:
<223> OTHER INFORMATION: synthetic oligonucleotide nitrWFR1-Sfi
<220> FEATURE:
<221> NAME/KEY: misc_feature
<222> LOCATION: (19)..(19)
<223> OTHER INFORMATION: n = a, c, g, or t.

<400> SEQUENCE: 12
gactggccga ggcggcccnc graacca         27

<210> SEQ ID NO 13
<211> LENGTH: 27
<212> TYPE: DNA
<213> ORGANISM: Artificial Sequence
<220> FEATURE:
<223> OTHER INFORMATION: synthetic oligonucleotide nitrWFR2-Sfi

<400> SEQUENCE: 13
gactggccga ggcggcccyc traacca         27

<210> SEQ ID NO 14
<211> LENGTH: 27
<212> TYPE: DNA
<213> ORGANISM: Artificial Sequence
<220> FEATURE:
<223> OTHER INFORMATION: synthetic oligonucleotide nitrWFK-Sfi

<400> SEQUENCE: 14
gactggccga ggcggcccyt traacca         27

<210> SEQ ID NO 15
<211> LENGTH: 27
<212> TYPE: DNA
<213> ORGANISM: Artificial Sequence
<220> FEATURE:
<223> OTHER INFORMATION: synthetic oligonucleotide CXV-Sfi
<220> FEATURE:
<221> NAME/KEY: misc_feature
<222> LOCATION: (19)..(19)
<223> OTHER INFORMATION: n = a, c, g, or t.
<220> FEATURE:
<221> NAME/KEY: misc_feature
<222> LOCATION: (22)..(24)
<223> OTHER INFORMATION: n = a, c, g, or t.

<400> SEQUENCE: 15
gactggccga ggcggcccna cnnnrca         27

<210> SEQ ID NO 16
<211> LENGTH: 5
<212> TYPE: PRT
<213> ORGANISM: Artificial Sequence
<220> FEATURE:
<223> OTHER INFORMATION: Amino acid motif

<400> SEQUENCE: 16

Val Tyr Trp Phe Arg
1               5

<210> SEQ ID NO 17
<211> LENGTH: 4
<212> TYPE: PRT
<213> ORGANISM: Artificial Sequence
<220> FEATURE:
<223> OTHER INFORMATION: Amino acid motif

<400> SEQUENCE: 17

-continued

```
Val Tyr Trp Phe
1

<210> SEQ ID NO 18
<211> LENGTH: 4
<212> TYPE: PRT
<213> ORGANISM: Artificial Sequence
<220> FEATURE:
<223> OTHER INFORMATION: Amino acid motif

<400> SEQUENCE: 18

Tyr Trp Phe Arg
1

<210> SEQ ID NO 19
<211> LENGTH: 4
<212> TYPE: PRT
<213> ORGANISM: Artificial Sequence
<220> FEATURE:
<223> OTHER INFORMATION: Amino acid motif

<400> SEQUENCE: 19

Tyr Trp Phe Lys
1
```